(12) United States Patent
Shiba et al.

(10) Patent No.: US 7,498,403 B2
(45) Date of Patent: Mar. 3, 2009

(54) PEPTIDES CAPABLE OF BINDING TO TITANIUM SILVER SILICONE

(75) Inventors: Kiyotaka Shiba, Tokyo (JP); Kenichi Sano, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 252 days.

(21) Appl. No.: 10/566,535

(22) PCT Filed: Jul. 30, 2004

(86) PCT No.: PCT/JP2004/011319

§ 371 (c)(1),
(2), (4) Date: Apr. 27, 2006

(87) PCT Pub. No.: WO2005/010031

PCT Pub. Date: Feb. 3, 2005

(65) Prior Publication Data

US 2007/0112174 A1 May 17, 2007

(30) Foreign Application Priority Data

Jul. 30, 2003 (JP) ............................. 2003-282509

(51) Int. Cl.
*A61K 38/08* (2006.01)
*A61K 38/10* (2006.01)
(52) U.S. Cl. .................. 530/327; 530/328; 530/329
(58) Field of Classification Search .................. None
See application file for complete search history.

(56) References Cited

U.S. PATENT DOCUMENTS

| | | | |
|---|---|---|---|
| 6,833,447 B1 * | 12/2004 | Goldman et al. | 536/23.1 |
| 7,214,786 B2 * | 5/2007 | Kovalic et al. | 536/23.6 |
| 2003/0073104 A1 | 4/2003 | Belcher et al. | |
| 2003/0185870 A1 | 10/2003 | Grinstaff et al. | |
| 2006/0035223 A1 * | 2/2006 | Naik et al. | 435/6 |
| 2006/0051395 A1 * | 3/2006 | Beyer et al. | 424/423 |

FOREIGN PATENT DOCUMENTS

| | | |
|---|---|---|
| JP | 10-338700 | 12/1998 |
| WO | WO 01/28605 A1 | 4/2001 |
| WO | WO 02/060506 A1 | 8/2002 |
| WO | WO 02/080186 | 10/2002 |
| WO | WO 03/029431 A2 | 4/2003 |
| WO | WO 03/078451 A2 | 9/2003 |

OTHER PUBLICATIONS

Rudinger "Characteristic of the amino acids as components of a peptide hormone sequence." (Peptide Hormones (Ed. J.A. Parson). University Park Press. Baltimore, 1976, pp. 1-7.*
Pitt et al. "Single amino acid substitution mutants of Klebsiella pneumoniae singma54 defective in transcription" Nuc. Ac. Res., 2000, 28, 4419-4427.*
Bradley et al. "Limits of Cooperativity in a Structurally Modular Protein: Response of the Notch Ankyrin Domain to Analogous Alanine Substitutions in Each Repeat" J. Mol. Biol., 2002, 324, 373-386.*
Flanagan et al. "Truncated staphyloccal nuclease is compact but disordered" Proc. Natl. Acad. Sci. USA, 1992, 89, 748-752.*
Schnog et al. "Sickle cell disease; a general overview" J. Med., 2004, 62, 364-374.*
Sawai et al. "Impact of single-residue mutations on the structure and function of ovispirin/novispirin antimicrobial peptides" Prot. Engin., 2002, 15, 225-232.*
"New acyclic peptide with metal trapping activity—exhibits in vivo metal transporting action and can be used as drug, diagnostic agent or functional material," *Derwent*, May 24, 1991, Abstract.
Goud, et al., "Selection of specific peptide ligands for immobilized metals using a phage displayed library: application to protein separation using IMAC," *Inter J Bio-Chroma* 3(2):123-136, 1997.
Patwardan, et al., "Phage-displayed libraries for the selection of optimal affinity peptides for protein purification using Ni-nitrilotriacetic acid chromatography," *Biotechnology Techniques* 12(6):421-424, 1998.
Wang Siqun, et al., "Peptides with selective affinity for carbon nanotubes," *Nature Materials* 2(3):196-200, 2003.
Zreiqat, et al., "Differentiation of human bone-derived cells grown on GRGDSP-peptide bound titanium surfaces," *Journal of Biochemical Materials Research* 64A(1):105-113, 2003.
Naik, et al., "Silica-precipitating peptides isolated from a combinatorial phage display peptide library," *Journal of Nanoscience and Nanotechnology* 2(1):95-100, 2002.
Supplementary Partial European Search Report for the related European national phase application No. 04771321.9 of the PCT Application No. PCT/JP2004/011319, actual completion of the European search date May 25, 2007; date of mailing Jun. 18, 2007.

(Continued)

*Primary Examiner*—Cecilia Tsang
*Assistant Examiner*—Christina Marchetti Bradley
(74) *Attorney, Agent, or Firm*—Morgan & Finnegan, LLP

(57) ABSTRACT

The present invention provides a peptide sequence, a phage, an artificial protein or a chimeric molecule having a binding ability to titanium, silver, silicon, necessary to confer higher capacity of titanium, silver, silicon material with the use of soft matters, or to provide a complex of a peptide, a phage, an artificial protein or a chimeric molecule, and titanium, having the peptide sequence and functional peptide sequence. By bringing into contact a population of phage wherein said phage of said population collectively express a library of different peptide sequence, recovering titanium bound to phage particles via peptide sequence by centrifugation, proliferating the obtained phage particles in bacteria, and repeating panning operation and concentrating titanium binding phage clones. Among the phage clones, peptide RKLP-DAPGMHTW (SEQ ID NO: 3) and the like is identified. As for a peptide having a binding ability to titanium, silver, silicon, RKLPDA (SEQ ID NO: 1) or RALPDA (SEQ ID NO: 2) can be exemplified.

38 Claims, 19 Drawing Sheets

OTHER PUBLICATIONS

Supplementary European Search Report for the related European national phase application No. 04771321.9 of the PCT Application No. PCT/JP2004/011319, actual completion of the European search date May 25, 2007; date of mailing Sep. 13, 2007.

Naik et al, "Biomimetic Synthesis and patterning of silver nanoparticles," Nature Materials, vol. 1, pp. 169-172; Nov. 2002.

Whaley et al, "Selection of peptides with semiconductor binding specificity for directed nanocrystal assembly," Nature, vol. 408, pp. 665-668, Jun. 8, 2000.

Sano et al, "A Hexapeptide Motif that Electrostatically Binds to the Surface of Titanium," J. Am. Chem. Soc., vol. 125, No. 47, pp. 14234-14235, Nov. 26, 2003, published on web Oct. 30, 2003.

* cited by examiner

Fig. 3

| | | |
|---|---|---|
| e3-2-2 | (SEQ ID NO: 16) | LDTTNVSGPMSS |
| e3-2-3 | (SEQ ID NO: 3) | RKLPDAPGMHTW |
| e3-2-4 | (SEQ ID NO: 3) | RKLPDAPGMHTW |
| e3-2-5 | (SEQ ID NO: 17) | SYRLPVYLHALL |
| e3-2-6 | (SEQ ID NO: 3) | RKLPDAPGMHTW |
| e3-2-7 | (SEQ ID NO: 3) | RKLPDAPGMHTW |
| e3-2-8 | (SEQ ID NO: 18) | SDPNQDWRRTTP |
| e3-2-9 | (SEQ ID NO: 3) | RKLPDAPGMHTW |
| e3-2-10 | (SEQ ID NO: 3) | RKLPDAPGMHTW |
| e3-2-12 | (SEQ ID NO: 19) | LPSQLLSQVNLT |
| e3-2-13 | (SEQ ID NO: 3) | RKLPDAPGMHTW |
| e3-2-14 | (SEQ ID NO: 3) | RKLPDAPGMHTW |
| e3-2-15 | (SEQ ID NO: 3) | RKLPDAPGMHTW |
| e3-2-16 | (SEQ ID NO: 3) | RKLPDAPGMHTW |
| e3-2-17 | (SEQ ID NO: 3) | RKLPDAPGMHTW |
| e3-2-18 | (SEQ ID NO: 3) | RKLPDAPGMHTW |
| e3-2-19 | (SEQ ID NO: 20) | LCANNTTSVHPP |
| e3-2-20 | (SEQ ID NO: 3) | RKLPDAPGMHTW |
| e3-2-21 | (SEQ ID NO: 21) | MQMEGKPTLTLR |
| e3-2-22 | (SEQ ID NO: 3) | RKLPDAPGMHTW |
| e3-2-23 | (SEQ ID NO: 3) | RKLPDAPGMHTW |
| e3-2-25 | (SEQ ID NO: 3) | RKLPDAPGMHTW |
| e3-2-29 | (SEQ ID NO: 22) | STLKNPINLLAN |
| e3-2-30 | (SEQ ID NO: 3) | RKLPDAPGMHTW |
| e3-2-31 | (SEQ ID NO: 3) | RKLPDAPGMHTW |
| e3-2-33 | (SEQ ID NO: 3) | RKLPDAPGMHTW |
| e3-2-34 | (SEQ ID NO: 3) | RKLPDAPGMHTW |
| e3-2-36 | (SEQ ID NO: 3) | RKLPDAPGMHTW |
| e3-2-39 | (SEQ ID NO: 3) | RKLPDAPGMHTW |
| e3-2-40 | (SEQ ID NO: 3) | RKLPDAPGMHTW |
| e3-2-41 | (SEQ ID NO: 3) | RKLPDAPGMHTW |
| e3-2-42 | (SEQ ID NO: 3) | RKLPDAPGMHTW |
| e3-2-43 | (SEQ ID NO: 23) | SCHVWYDSCSSP |
| e3-2-45 | (SEQ ID NO: 3) | RKLPDAPGMHTW |
| e3-2-46 | (SEQ ID NO: 3) | RKLPDAPGMHTW |
| e3-2-47 | (SEQ ID NO: 3) | RKLPDAPGMHTW |
| e3-2-48 | (SEQ ID NO: 3) | RKLPDAPGMHTW |
| e3-2-49 | (SEQ ID NO: 3) | RKLPDAPGMHTW |
| e3-2-50 | (SEQ ID NO: 22) | STLKNPINLLAN |
| e3-2-51 | (SEQ ID NO: 3) | RKLPDAPGMHTW |
| e3-2-52 | (SEQ ID NO: 3) | RKLPDAPGMHTW |
| e3-2-55 | (SEQ ID NO: 24) | QDMIRTSALMLQ |
| e3-2-56 | (SEQ ID NO: 3) | RKLPDAPGMHTW |

Fig. 4

| | | |
|---|---|---|
| e3-4-2 | (SEQ ID NO: 25) | CTSPTSVDC |
| e3-4-3 | (SEQ ID NO: 26) | CTPSPHQGC |
| e3-4-4 | (SEQ ID NO: 27) | CHTAPLPRC |
| e3-4-5 | (SEQ ID NO: 26) | CTPSPHQGC |
| e3-4-6 | (SEQ ID NO: 28) | CHGATPQNC |
| e3-4-7 | (SEQ ID NO: 29) | CSGHNPTHC |
| e3-4-8 | (SEQ ID NO: 25) | CTSPTSVDC |
| e3-4-9 | (SEQ ID NO: 26) | CTPSPHQGC |
| e3-4-11 | (SEQ ID NO: 30) | CPMWQAQQC |
| e3-4-12 | (SEQ ID NO: 31) | CGVYSMSHC |
| e3-4-13 | (SEQ ID NO: 32) | CDMLTPRSC |
| e3-4-15 | (SEQ ID NO: 25) | CTSPTSVDC |
| e3-4-16 | (SEQ ID NO: 33) | CLRLQSQDC |
| e3-4-17 | (SEQ ID NO: 34) | CQITWHHTC |
| e3-4-19 | (SEQ ID NO: 26) | CTPSPHQGC |
| e3-4-21 | (SEQ ID NO: 35) | CSAHHHDKC |
| e3-4-22 | (SEQ ID NO: 26) | CTPSPHQGC |
| e3-4-23 | (SEQ ID NO: 36) | CMTKNPLNC |
| e3-4-24 | (SEQ ID NO: 26) | CTPSPHQGC |
| e3-4-25 | (SEQ ID NO: 26) | CTPSPHQGC |
| e3-4-26 | (SEQ ID NO: 26) | CTPSPHQGC |
| e3-4-27 | (SEQ ID NO: 25) | CTSPTSVDC |
| e3-4-28 | (SEQ ID NO: 36) | CMTKNPLNC |
| e3-4-29 | (SEQ ID NO: 37) | CKTSLPTTC |
| e3-4-30 | (SEQ ID NO: 38) | CVSTYWKTC |
| e3-4-31 | (SEQ ID NO: 25) | CTSPTSVDC |
| e3-4-32 | (SEQ ID NO: 25) | CTSPTSVDC |

Fig. 6
A: Non-blocking
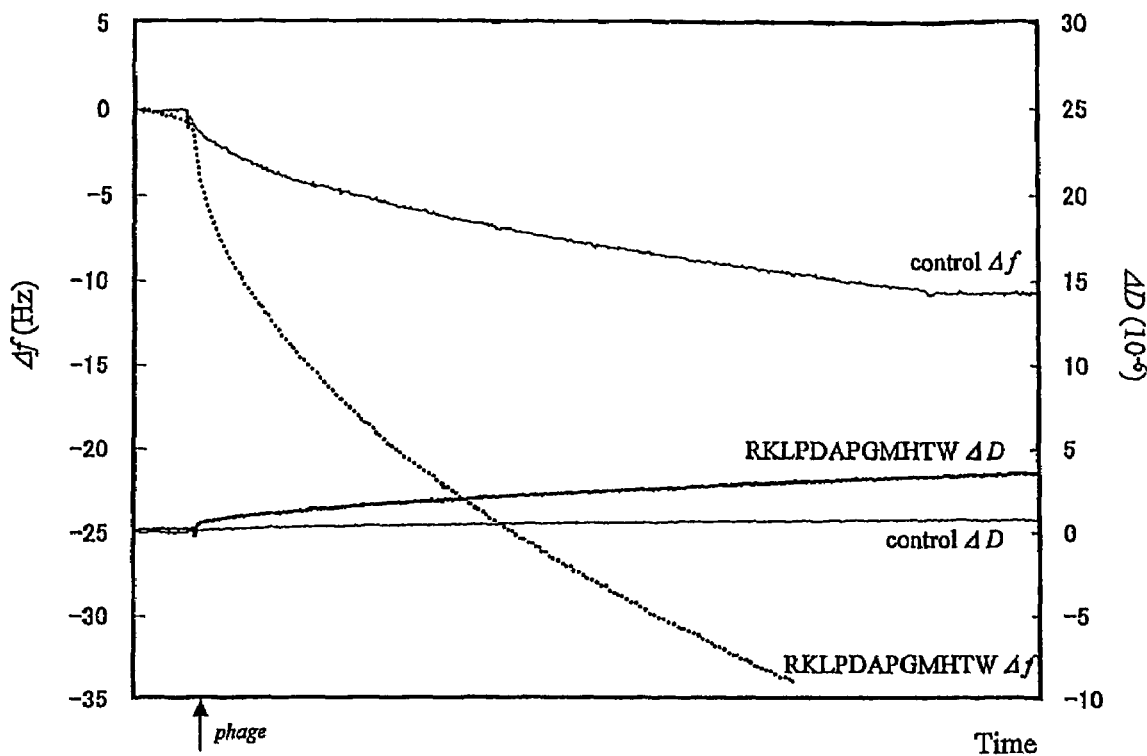
B: BSA blocking
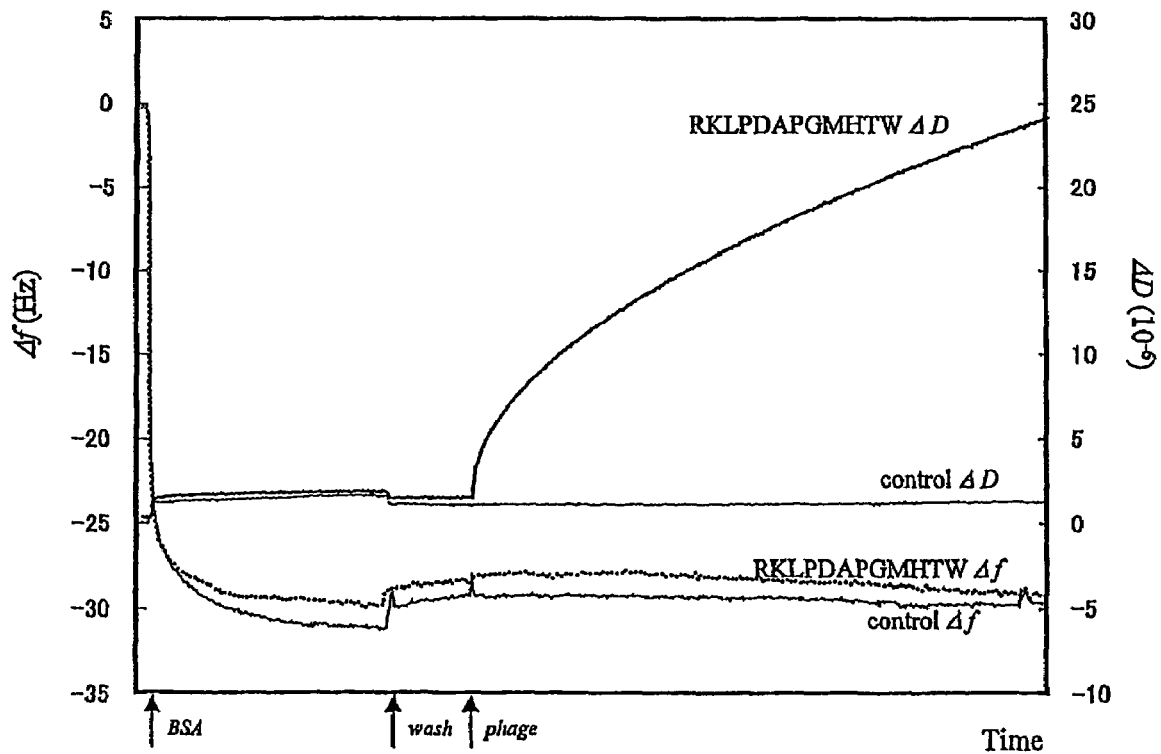

Fig. 7
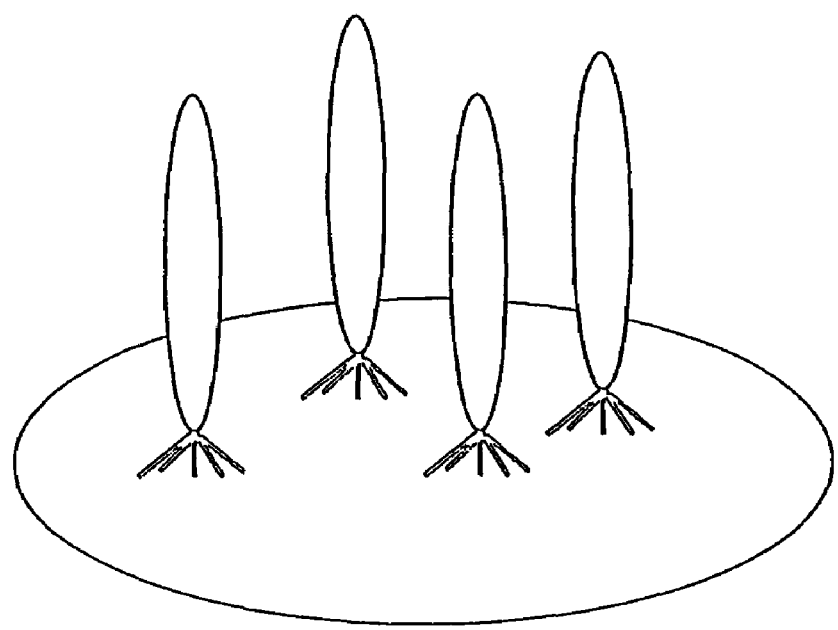
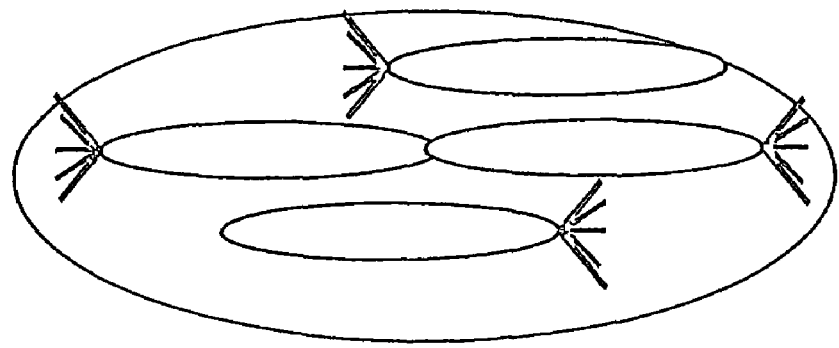

Fig. 8

| | |
|---|---|
| R1A (SEQ ID NO: 4): | AGGCAGCTTCGCAGAGTGAGAATAG |
| K2A (SEQ ID NO: 5): | CATCAGGCAGCGCCCGAGAGTGAG |
| L3A (SEQ ID NO: 6): | GGAGCATCAGGCGCCTTCCGAGAG |
| P4A (SEQ ID NO: 7): | CCGGGAGCATCAGCCAGCTTCCGAG |
| D5A (SEQ ID NO: 8): | ATCCCGGGAGCAGCAGGCAGCTTC |
| P7A (SEQ ID NO: 9): | GTATGCATCCCGGCAGCATCAGGCA |
| G8A (SEQ ID NO: 10): | AGTATGCATCGCGGGAGCATCAGG |
| M9A (SEQ ID NO: 11): | CCCCAAGTATGCGCCCCGGGAGCATC |
| H10A (SEQ ID NO: 12): | TCCACCCCAAGTAGCCATCCCGGGA |
| T11A (SEQ ID NO: 13): | TCCACCCCAAGCATGCATCCCGG |
| W12A (SEQ ID NO: 14): | AACCTCCACCCGCAGTATGCATC |
| | |
| Δ7-12F (SEQ ID NO: 51): | GGAGGATCCGCCGAAACTGTTGAAAGTTG |
| Δ7-12R (SEQ ID NO: 52): | GGGGGATCCTCCACCAGCATCAGGCAGCTTCCGAG |
| K2AΔ7-12R (SEQ ID NO: 53): | GGGGGATCCTCCACCAGCATCAGGCAGCGCCCGAG |
| | |
| Ala insert (SEQ ID NO: 54): | AGCATCAGGCAGCTTCCGTGCAGAGTGAGAATAGAAAGG |

PEPTIDES CAPABLE OF BINDING TO TITANIUM SILVER SILICONE

TECHNICAL FIELD

The present invention relates to a method for screening for titanium binding peptides; a peptide having a binding ability to titanium, silver and/or silicon; a complex of titanium, silver and/or silicon with a peptide, wherein a peptide having a binding ability to titanium, silver and/or silicon is bound to titanium, silver or silicon; an artificial protein wherein a peptide having a binding ability to titanium, silver and/or silicon is bound to a functional peptide or a functional protein; a complex of a titanium, silver or silicon with the artificial protein, wherein the artificial protein is bound to titanium, silver or silicon; a chimeric protein wherein a conjugate of a peptide having a binding ability to titanium, silver and/or silicon with a labeled substance or a peptide tag, or with a nonpeptide compound is bound; a complex of titanium, silver or silicon with a chimeric protein wherein the chimeric protein is bound to titanium, silver or silicon; a phage expressing a peptide having a binding ability to titanium, silver and/or silicon on the particle surface; a complex of titanium, silver or silicon with a phage wherein the phage is bound to titanium, silver or silicon; a method for refinement of a titanium surface, a silver surface or a silicon surface or for aligning titanium, by using a peptide having a binding ability to titanium, silver and/or silicon, an artificial protein with a binding ability to titanium, silver and/or silicon, a chimeric protein with a binding ability to titanium, silver and/or silicon, a phage with a binding ability to titanium, silver and/or silicon; a method for forming a silver particle or a silicon particle; or an implant material comprising a titanium-artificial protein complex as an active ingredient.

BACKGROUND ART

In 1952, Brànemark found out the Osseointegration phenomenon, in which titanium and bone were bound without mediating binding tissues, and with this as a turning point, implant made of pure titanium was clinically applied for the first time in 1965. A lot of implant treatment using Osseointegration phenomenon have been applied so far. However, a very long period of 3 to 6 months is required for titanium and bone to be bound. Heretofore, for the purpose of shortening this period by enhancing bone-affinity, many approaches such as redesigning hard matters being mainly mechanical material modification have been made, including modification to final surface treatment, vacuum evaporation of calcium or hydroxyapatite to titanium surface, or consideration of titanium alloy as a material, while no significant effect has been obtained so far. For example, in case of ceramics such as hydroxyapatite, there are problems such as reduction of coated layer or weakness to load due to physical characteristics. As for alloy, many cases have been considered so far, but in most of the cases, harmful tissue reactions have occurred, and therefore, only titanium and $Ti_6Al_4V$, being alloy thereof, is currently used.

Moreover, the relation between implant and surrounding mucosa is considered to be a scar tissue with small resistance to infection, which is different from that of tooth and gum. Therefore, in order to resolve this problem, approaches from hard matters have been considered as described in the above, including coating antibacterial agent to titanium surface. However, with such approaches from hard matters, improvement of anatomic/histological relationship between implant and surrounding mucosa are not considered.

Titanium is easily oxidized, and forms immediately dioxide in atmosphere and in water. As it is possible to degrade/detoxify almost all toxic substances by using photocatalytic activity of anatase crystals, which is one of titanium dioxide crystals, titanium is used for variously including degradation of bad smell such as sick house gas or acetaldehyde, or as anti-fungal agent. However, as the wavelength which anatase crystals can use is limited to the ultra-violet region, development of photocatalysts which can be used in a visible radiation region to awaited.

Furthermore, the following is proposed: a new implant containing osteopontin that can increase osseointegration rate and bone adhesion ratio, comprising an implant containing osteopontin in a formed state, wherein a material appropriate for use to a subject body in vivo is combined with an osteopontin in a releasable form (Published Japanese Translation of PCT International Publication No: 2002-500898); a technology controlling at a molecule level a construction of a metal compound to be bound, wherein in order to bind metal compound, and to provide a new protein, a protein fragment, a peptide or a derivative of a mutant thereof that is possible to bind metal compounds and to control the orientation or the sequence, a functional group having nitrilotriacetate construction is inserted to a characteristic stereo structure that the protein, the protein fragment, the peptide or the mutant thereof have (Japanese Laid-Open Patent Application No: 10-338700); or a method for preparing nanocrystals of semiconductors having specific crystal properties such as phase or configuration, by using self-organizing biological molecule modified so to have an amino acid oligomer that binds specifically to semiconductors (US Patent Application No. 2003/0073104 specification).

As mentioned above, when intending to confer higher capacity of titanium materials in the field of implant, not by modifying materials by hard matter, but with polymer such as protein being a soft matter that can bind flexibly to titanium surface, there is a problem that amino acid motif that recognizes/binds specifically to titanium surface does not exist in the nature. The object of the present invention is to provide a peptide sequence, a phage, an artifioial protein or a chimeric molecule with a binding ability to titanium necessary to confer higher capacity to titanium material with the use of soft matters, or a complex of a peptide, a phage, an artificial protein or a chimeric molecule having the peptide sequence and a functional peptide sequence, with titanium. Specifically, the present invention provides a functional titanium implant material wherein said peptide and a peptide or an artificial protein/a chimeric protein promoting calcification or bone growth/differentiation are bound to its surface, by which the osseointegration completes in a short period; or a functional titanium implant material wherein said peptide and a peptide or an artificial protein/a chimeric protein having high affinity to gum are bound to its surface, having a high resistance to bacterial infection, etc. Moreover, it provides a complex of the peptide or the artificial protein/the chimeric protein with oxidized titanium, or a complex of the complex with a low molecule compound such as chromophore, having a photocatalystic ability even in a visible radiation region, and a dioxide titanium pigment, wherein a chimeric protein/an artificial protein comprising the peptide and collagen gentle to skin, etc., are bound to its surface.

The present inventors made a keen study to solve the above problems. They brought into contact a population of phage wherein said phage of said population collectively express a library of different peptide sequences to titanium metal in an aqueous solution, recovered titanium bound to phage particles via peptide sequence by centrifugation, proliferated the obtained phage particles bound to titanium in *E. coli*, and repeated a panning operation comprising the contact of titanium with the proliferated titanium binding phage expressing a peptide sequence on phage particles and concentrating phage clones binding to titanium and obtained a phage library that might express a titanium binding peptide that recognizes specifically titanium.

The obtained phage library was cloned to examine the amino acid sequence expressed. By repeating the panning operation, it can be estimated that clones expressing sequences that can strongly bind to especially titanium had a major population in the phage library. The present inventors found that among 43 phage clones there were 33 clones expressing RKLPDAPGMHTW (peptide comprising an amino acid sequence shown in SEQ ID NO; 3), and that the binding ability to titanium of the phage clones expressing a peptide comprising an amino acid sequence shown in SEQ ID NO: 3 was much higher than that of the phage clone expressing a peptide comprising amino acid sequences shown in SEQ ID NOs: 16 to 38.

It is necessary to investigate whether the obtained clones expressing a peptide comprising an amino acid sequence shown in SEQ ID No: 3 are bound to titanium via the sequence they are expressing. It is possible to confirm whether the binding of the phage clone expressing a peptide comprising an amino acid sequence shown in SEQ ID NO:3 to titanium is bound specifically via the expressing sequence, with the use of QCM-D300 (Q-sense AB, Goeteborg), a device for quantification of interaction with a quartz crystal microbalance that can measure dissipation simultaneously. When a molecule elongated lengthwise like a phage, is bound perpendicularly to a crystal microbalance sensor, the viscoelasticity measured by dissipation increases significantly, while the frequency showing the binding level decreases. Further, even it is a very long elongated molecule, no significant increase of viscoelasticity is observed in contrast to the decrease of frequency, when bound horizontally to the side on which a crystal microbalance sensor was mounted. Actually, a result showing that a phage clone presenting a peptide comprising an amino acid sequence shown in SEQ ID NO: 3 was bound perpendicularly to titanium surface was obtained. It is probably the first example in the world, to have examined the binding form of a phage, by using a device for quantification of interaction with a quartz crystal microbalance, and it showed that this method was very useful for the analysis of a phage bound to the solid surface.

The titanium surface is oxidized immediately in water, and a hydroxy group binds to titanium atoms. It is estimated that the bound hydroxy group separates into a hydroxy group that bridges between two titanium atoms and a terminal hydroxy group bound with one titanium atom. As the polarity of the bridging hydroxy group and that of the terminal hydroxy group are different, they have a different pK. It is estimated that the bridging hydroxy group acts as an acid, and that the terminal hydroxy group acts as a base. It would be possible to control the binding of titanium and peptide by investigating how a peptide comprising an amino acid sequence shown in SEQ ID NO: 3 is bound specifically to titanium surface.

Generally, investigation of specificity of a peptide motif is conducted by identification of a residue playing an important role to the function due to the introduction of point mutation, or by refinement of functional region by an analysis of deletion mutant. In the former one, functional analysis of a series of alanine-substituted point mutants called alanine scanning is often performed. Substitution to alanine wherein methyl group has only one small side chain, and that has no charge, is thought to impair the function of the side chain of the amino acid residue. Alanine scanning was performed for the phage clone expressing a peptide comprising an amino acid sequence shown in SEQ ID NO: 3. A series of point-mutated phage clones expressing a peptide comprising amino acid sequences shown in SEQ ID NOs: 4 to 14 was prepared and the binding ability to titanium of each clone was examined. As a result, the binding ability of the point mutant to the 4th proline was the most significantly impaired, among those examined this time. Proline plays a role to curve widely the main chain of peptide or protein, similar to glycine. From this result, it was strongly suggested that the curve of the main chain in the 4th proline plays an important role for binding the peptide comprising an amino acid sequence shown in SEQ ID NO: 3 to titanium. Furthermore, as the binding ability of the point mutant to the 1st arginine and 5th aspartic acid among the amino acids being charged at the side chain was significantly impaired, it was suggested that these residues are mutually acted with the positive and negative charge of the titanium surface.

As a result of alanine scanning, a result supporting that the former part of SEQ ID NO: 2, region of SEQ ID NO: 1, plays an important role in the binding to titanium, was obtained. Therefore, a deletion mutant wherein 7th to 12th peptides comprising an amino acid sequence shown in SEQ ID NO: 3 are deleted, that is a phage clone expressing a peptide comprising an amino acid sequence shown in SEQ ID NO: 1 was prepared and the binding ability to titanium was investigated. As the binding ability to titanium was not affected by the deletion, it has been clarified that the amino acid sequence part shown in SEQ ID NO: 1 had a sufficient titanium binding ability.

When the peptide sequence shown in SEQ ID NO: 3 binds to titanium, the importance of the positive charge of the side chain of the 1st arginine is as described above, while there is still a possibility that it cooperates with an amino group at amino terminal of the main chain for binding to titanium. Therefore, an insert mutant (SEQ ID NO: 15) wherein alanine is inserted to amino terminal of the amino acid sequence shown in SEQ ID NO: 3 was prepared and the binding ability to titanium was investigated. As a result, increase of the binding ability to titanium was observed. As for the reason of the Increase of the binding ability, it can be considered that repulsion between the positive charge of the side chain of 2nd lysine of SEQ ID NO: 3 and the positive charge of an amino group at amino terminal of the main chain decreases due to the insertion of amino acid of one residue, and thus the structure of a peptide comprising an amino acid sequence shown in SEQ ID NO: 15 became more stable. Furthermore, this result shows that it is not always necessary that arginine is at the amino terminal when a peptide comprising an amino acid sequence shown in SEQ ID NO: 3 binds to titanium. This is an important knowledge showing that there is no limitation for primary construction as for the placement of SEQ ID NO: 1 or 3, when preparing a chimeric protein, an artificial protein or a synthetic peptide binding to titanium.

It is known that a number of hydroxy groups bind to titanium surface by hydrogen peroxide treatment. As it is mentioned above, it is thought that the interaction between a peptide comprising an amino acid sequence shown in SEQ ID NO: 1, 3 and titanium surface is dominated by the electrostatic interaction between the side chains of 1st arginine and 5th aspartic acid of SEQ ID NO: 1, 3 and the charge of the hydroxyl group bound to titanium. There is a possibility that the binding level of titanium and peptide can be controlled, if it would be possible to control the amount of hydroxyl group binding to titanium. In fact, the binding ability of the phage clone expressing SEQ ID NO: 3, treated with hydrogen peroxide, to titanium increased. This shows that by further adding hydroxy group to titanium surface by hydrogen peroxide treatment, it is possible to increase the binding level of the phage clone expressing SEQ ID NO: 3, the peptide of SEQ ID NO: 3, and the artificial protein/chimeric protein including thereof. Furthermore, by removing hydroxy group from titanium surface, it is expected to be possible to decrease the binding level of the phage clone expressing a peptide comprising an amino acid sequence shown in SEQ ID NO: 3, the peptide of SEQ ID NO: 3 and the artificial protein/chimeric protein including thereof. As for the method for removing hydroxy group from titanium surface, sodium fluoride treatment can be exemplified. By combining these methods, it is expected to be possible to control the binding level of the phage clone expressing SEQ ID NO: 3, the peptide of SEQ ID NO: 3, or the artificial protein/chimeric protein including thereof, to titanium.

Moreover, by investigating the binding specificity of peptides with a binding ability to titanium to metal materials, it was found they bind selectively to silver, silicon, besides titanium, and that they do not bind to gold, platinum, copper, iron, tin, zinc, chrome, etc. By using this binding specificity of metal materials, it might be possible to develop a certain pattern on gold basis of the functional compounds via titanium binding peptide, by for example performing patterning on gold basis with titanium, and by adding functional compounds, for example titanium binding peptide conjugating semiconductor nano particles, or artificial protein/chimeric protein including thereof.

The present inventors have thus completed the present invention according to the above knowledge.

DISCLOSURE OF THE INVENTION

In other words, the present invention relates to a method for screening for titanium binding peptides comprising contacting titanium with a population of phage wherein said phage of said population collectively express a library of different peptide sequence; recovering titanium bound to phage particles via peptide sequence from said population by centrifugation; proliferating the obtained titanium binding phage particles in bacteria; and repeating a panning operation comprising the contact of titanium with the proliferated titanium binding phage expressing a peptide sequence on phage particles and concentrating proliferating titanium binding phage clones ("1"); a titanium binding peptide obtained by the method for screening according to "1" ("2"); a titanium binding peptide comprising an amino acid sequence shown in SEQ ID NO: 1 ("3"); a titanium binding peptide comprising an amino acid sequence shown in SEQ ID NO: 1, wherein at least one amino acid is deleted, substituted or added in the amino acid sequence ("4"); the titanium binding peptide according to "4", wherein the 1, 4 and 5th amino acid residues of the amino acid sequence shown in SEQ ID NO: 1 are conserved ("5"); the titanium binding peptide according to "5", comprising an amino acid sequence shown in SEQ ID NO: 2 wherein the 2nd lysine is substituted by alanine ("6"); a titanium binding peptide comprising an amino acid sequence shown in SEQ ID NO: 3 ("7"); a titanium binding peptide comprising an amino acid sequence shown in SEQ ID NO; 3, wherein at least one amino acids is deleted, substituted or added in the amino acid sequence ("8"); the titanium binding peptide according to "8", wherein the 1, 4 and 5th amino acid residues of the amino acid sequence shown in SEQ ID NO: 3 are conserved ("9"); the titanium binding peptide according to "8", comprising amino acid sequences shown in SEQ ID NOs: 4 to 14, wherein the 1 to 5th and 7 to 12th amino acid residues are substituted by alanine, respectively ("10"); the titanium binding peptide according to "8" or "9", comprising an amino acid sequence shown in SEQ ID NO: 15, wherein alanine is added/inserted to the N terminal of the amino acid sequence shown in SEQ ID NO: 3 ("11"); the titanium binding peptide comprising amino acid sequences shown in SEQ ID NOs: 16 to 24 ("12"); a titanium binding peptide comprising amino acid sequences shown in SEQ ID NOs: 16 to 24, wherein at least one amino acid is deleted, substituted or added in the amino acid sequence. ("13"); a titanium binding peptide comprising an amino acid sequence shown in SEQ ID NOs: 25 to 38 ("14"); a titanium binding peptide comprising amino acid sequences shown in SEQ ID NOs: 25 to 38 wherein at least one amino acid is deleted, substituted or added in the amino acid sequence ("15"); the titanium binding peptide according to any one "2" to "15", being chemically modified ("16"); the titanium binding peptide according to any one "2" to "16", wherein titanium is metal titanium, titanium alloy or titanium dioxide ("17"); a titanium-peptide complex, wherein the titanium binding peptide according to any one of "2" to "16" is bound to titanium ("18"); an titanium binding artificial protein being a conjugate of the titanium binding peptide according to any one of "2" to "16", with a functional peptide or a functional protein ("19"); the artificial protein according to "19", wherein the functional peptide or the functional protein is a peptide or a protein that cooperates with a titanium binding peptide to form a two-dimensional crystalline by self-assembly ("20"); the artificial protein according to "19", wherein the functional peptide or the functional protein is a peptide or a protein comprising a peptide sequence having a cell-recognizing ability such as cell adhesion ability ("21"); a titanium-artificial protein complex, wherein the artificial protein according to any one of "19" to "21" is bound to titanium ("22"); a titanium binding chimeric protein being a conjugate of the titanium binding peptide according to any one of "2" to "17", with a labeled substance or a peptide tag, or with a conjugate with a nonpeptide compound ("23"); a titanium-chimeric protein complex, wherein the chimeric protein according to "23" is bound to titanium ("24"); a titanium binding phage expressing the titanium binding peptide according to any one of "2" to "17" on the particle surface ("25"); a titanium-phage complex, wherein the phage according to "25" is bound to titanium ("26"); a method for refinement of a titanium surface or for forming a titanium particle, wherein the titanium binding peptide according to any one of "2" to "17" is used ("27"); a method for refinement of a titanium surface, for forming a titanium particle, or for aligning titanium particles, wherein the titanium binding artificial protein according to any one of "19" to "21" is used ("28"); a method for refinement of a titanium surface or for forming a titanium particle, wherein the titanium binding chimeric protein according to "23" is used ("29"); a method for aligning titanium or for forming a titanium particle, wherein the titanium binding phage according to "25" is used ("30"); an implant material comprising the titanium-artificial protein complex according to "22" as an active ingredient ("31").

Furthermore, the present invention relates to a silver binding peptide, comprising an amino acid sequence shown in SEQ ID NO: 1 ("32"); a silver binding peptide comprising an amino acid sequence shown in SEQ ID NO: 1, wherein at least one amino acid is deleted, substituted or added in the amino acid sequence ("33"); the silver binding peptide according to "33", wherein the 1, 4 and 5th amino acid residues of the amino acid sequence shown in SEQ ID NO: 1 are conserved ("34"); the silver binding peptide according to "34", comprising an amino acid sequence shown in SEQ ID NO: 2, wherein the 2nd lysine is substituted by alanine ("35"); a silver binding peptide comprising an amino acid sequence shown in SEQ ID NO: 3 ("36"); a silver binding peptide comprising an amino acid sequence shown in SEQ ID NO: 3, wherein at least one amino acid is deleted, substituted or added in the amino acid sequence ("37"); the silver binding peptide according to any one of "32" to "37", being chemically modified ("38"); a silver-peptide complex, wherein the silver binding peptide according to any one of "32" to "38" is bound to silver ("39"); an silver binding artificial protein being a conjugate of the silver binding peptide according to any one of "32" to "38", with a functional peptide or a functional protein ("40"); a silver-artificial protein complex, wherein the artificial protein according to "40" is bound to silver ("41"); a silver binding chimeric protein being a conjugate of the silver binding peptide according to any one of "32" to "38", with a labeled substance or a peptide tag, or with a conjugate with a nonpeptide compound ("42"); a silver-chimeric protein complex, wherein the chimeric protein according t "42" is bound to silver ("43"); a silver binding phage expressing the silver binding peptide according to any one of "32" to "38" on the particle surface ("44"); a silver-phage complex, wherein the phage according to "44" is bound to silver ("45"); a method for refinement of a silver surface or for forming a silver particle, wherein the silver binding peptide according to any one of "32" to "38" is used ("46"); a method for refinement of a silver surface, for forming a silver particle, or for aligning silver, wherein the silver binding artificial protein according to "40" is used ("47"); a method for refinement of a silver surface or forming a silver particle, wherein the silver binding chimeric protein according to "42" is used ("48"); a method for forming a silver particle or for aligning silver, wherein the silver binding phage according to "44" is used ("49"); a silicon binding peptide comprising an amino acid sequence shown in SEQ ID NO: 1 ("50"); a silicon binding peptide comprising an amino acid sequence shown in SEQ ID NO: 1, wherein at least one amino acids is deleted, substituted or added in the amino acid sequence ("51"); the silicon binding peptide according to "49", wherein the 1, 4 and 5th amino acid residues of the amino acid sequence shown in SEQ ID NO: 1 are conserved ("52"); the silicon binding peptide according to "50", comprising an amino acid sequence shown in SEQ ID NO: 2, wherein the 2nd lysine is substituted by alanine ("53"); a silicon binding peptide comprising an amino acid sequence shown in SEQ ID NO: 3 ("54"); a silicon binding peptide comprising an amino acid sequence shown in SEQ ID NO: 3, wherein at least one amino acid is deleted, substituted or added in the amino acid sequence ("55"); the silicon binding peptide according to any one of "50" to "56", being chemically modified ("56"); a silicon-peptide complex, wherein the silicon binding peptide according to any one of "50" to "56" is bound to silicon ("57"); an silicon binding artificial protein being a conjugate of the silicon binding peptide according to any one of "50" to "56", with a functional peptide or a functional protein ("58"); a silicon-artificial protein complex, wherein the artificial protein according to "58" is bound to silicon ("59"); a silicon binding chimeric protein, being a conjugate of the silicon binding peptide according to any one of "50" to "56", with a labeled substance or a peptide tag, or being a conjugate with a nonpeptide compound ("60"); a silicon-chimeric protein complex wherein the chimeric protein according to "60" is bound to silicon ("61"); a silicon binding phage expressing the silicon binding peptide according to any one of "50" to "56" on the particle surface ("62"); a silicon-phage complex, wherein the phage according to "62" is bound to silicon ("63"); a method for refinement of a silicon surface or for forming a silicon particle, wherein the silicon binding peptide according to any one of "50" to "56" is used ("64"); a method for refinement of a silicon surface, for forming a silicon particle, or for aligning silicon, wherein the silicon binding artificial protein according to "58" is used ("65"); a method for refinement of a silicon surface or for forming a silicon particle, wherein the silicon binding chimeric protein according to "60" is used ("66"); a method for forming a silicon particle or for aligning silicon, wherein the silicon binding phage according to "62" is used ("67"); a method using the titanium binding peptide according to any one of "2" to "17", the silver binding peptide according to any one of "32" to "38", or the silicon binding peptide according to any one of "50" to "56" as a probe of atomic force microscope (AFM) ("68").

The vertical axis represents the value of the eluted phage titer divided by the phage titer and shown in logarithmic. The number of the horizontal axis represents the number of times of panning.

Figure 2:
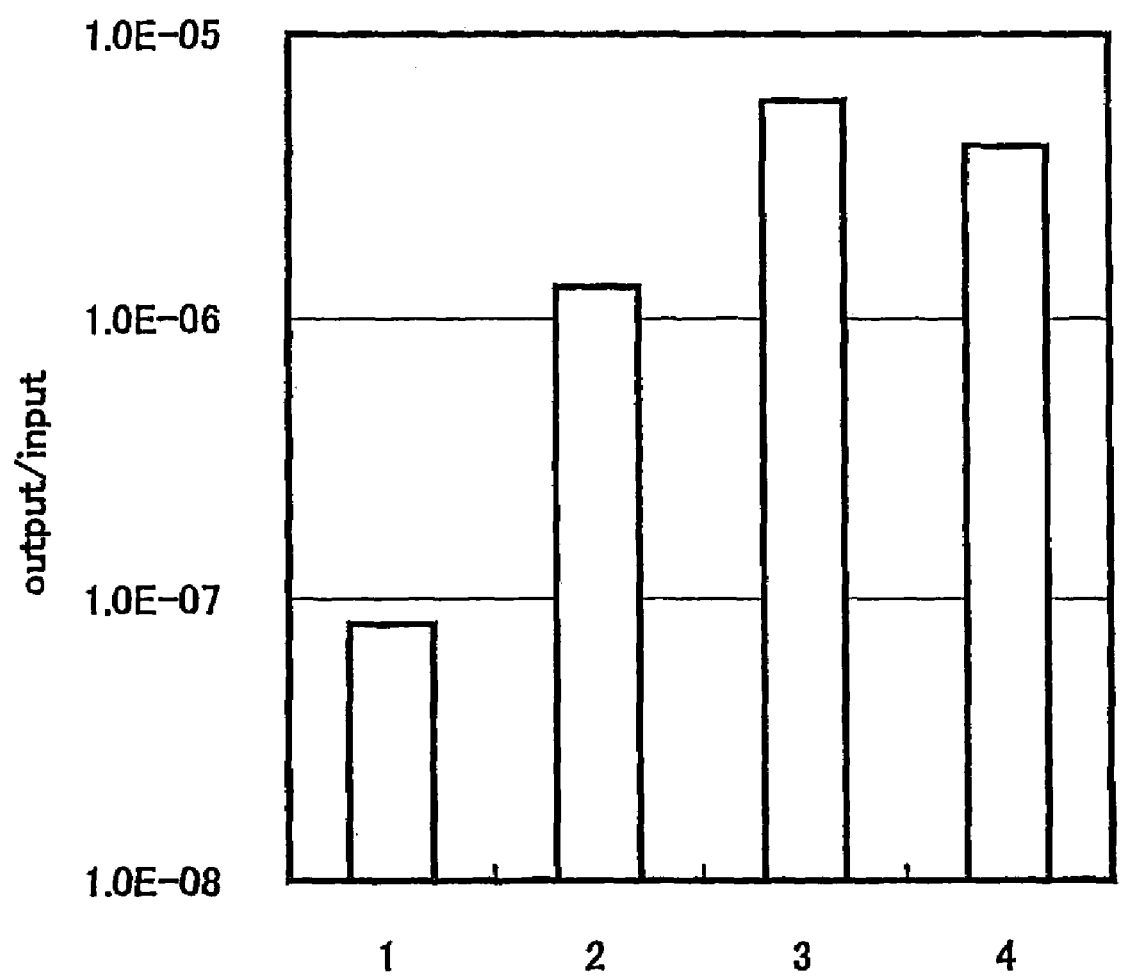

FIG. 2 is a picture showing the result of panning titanium particles by using C7C phage library.

The vertical axis represents the value of the eluted phage titer divided by the phage titer and shown in logarithmic. The number of the horizontal axis represents the number of times of panning.

FIG. 3 is a picture showing an amino acid sequence of a peptide expressed by the obtained clone after repeating 3 times the panning of titanium particles by using D-12 phage library.

The most left part shows the clone name, and the expressing sequence is shown beside by a single letter notation of the amino acid. The amino acid sequences of the peptides shown in FIG. 3 correspond to SEQ ID NOs: 3 and 16 to 24.

FIG. 4 is a picture showing an amino acid sequence of a peptide expressed by the obtained clone after repeating 3 times the panning of titanium particles by using C7C phage library. The amino acid sequences of the peptides shown in FIG. 4 correspond to SEQ ID NOs: 3 and 25 to 38.

The most left part shows the clone name, and the expressing sequence is shown beside by a single letter notation of the amino acid. The amino acid sequence herein shown comprise at both ends, a cysteine residue having a thiol group necessary for the expressing sequence of C7C library to be cyclic.

Figure 5:
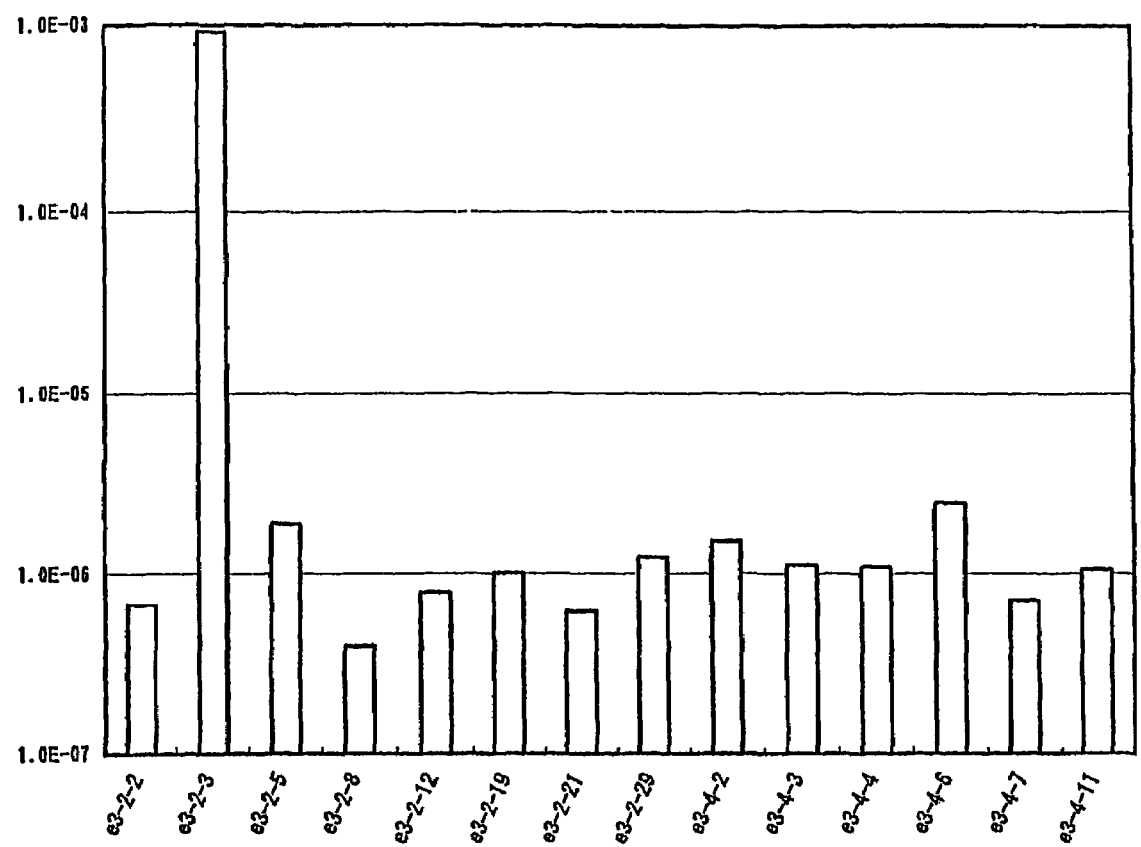

FIG. 5 is a picture showing the examination result of the binding ability of the cloned phage to titanium.

The vertical axis represents the value of the eluted phage titer divided by the phage titer and shown in logarithmic. The horizontal axis represents each phage clone shown in FIGS. 3 and 4.

FIG. 6 is a picture showing the analysis result of the binding condition of phage clone expressing the peptide shown in SEQ ID NO: 3 to titanium surface by using a device for analysis of interaction of biomolecule with a quartz crystal microbalance, QCM-D300.

FIG. 7 is a picture showing a pattern diagram of the binding condition of the phage on the titanium-quartz crystal microbalance sensor.

The binding of the phage clone to titanium surface by using QCM-D300 is shown schematically. The upper picture shows the binding condition when the sensor is blocked with BSA, and the bottom one shows the binding condition without blocking.

FIG. 8 is a picture showing the base sequences (SEQ ID NOs: 4 to 14 )of the primer used in the Examples.

The "alphabet-number-alphabet" shown in the left of the first paragraph of the figure, represents the mutant name prepared by using the primer. The origin of the name is as follows: sequence e3-2-3 (SEQ ID NO: 3) is represented by a single letter notation of the amino acid, the position of the amino acid residue from the amino terminal is represented by a number, and the last letter "A" shows the substitution by alanine. For example, P4A represents a primer used to substitute the 4th praline from N terminal of SEQ ID NO: 3 by alanine.

Next, Δ7-12F (SEQ ID NO: 51), Δ7-12R (SEQ ID NO: 52) and K2AΔ7-12R (SEQ ID NO: 53) are primers used to prepare deletion mutants explained in Example 5. They were used to PCR, with the combination of Δ7-12F and Δ7-12R; Δ7-12F and K2AΔ7-12R.

Ala insert (SEQ ID NO: 54) is a primer used to prepare insert mutant explained in Example 6.

Figure 9:
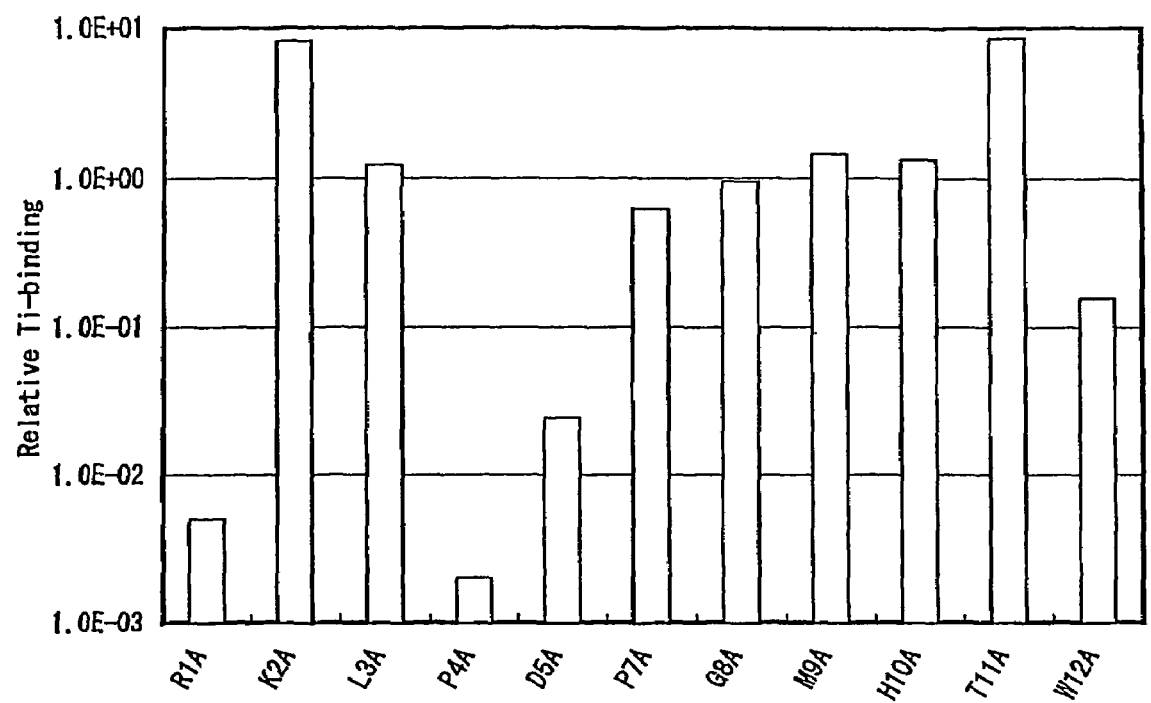

FIG. 9 is a picture showing the examination result of the influence of the point mutation on the binding ability of phage clone expressing a peptide shown in SEQ ID NOs: 4 to 14 to titanium.

The vertical axis represents the value of binding ability of the point mutant shown in logarithmic, by fixing the binding ability of the phage expressing a peptide shown in SEQ ID NOs: 4 to 14 to titanium to 1; the horizontal axis represents each point mutant.

Figure 10:
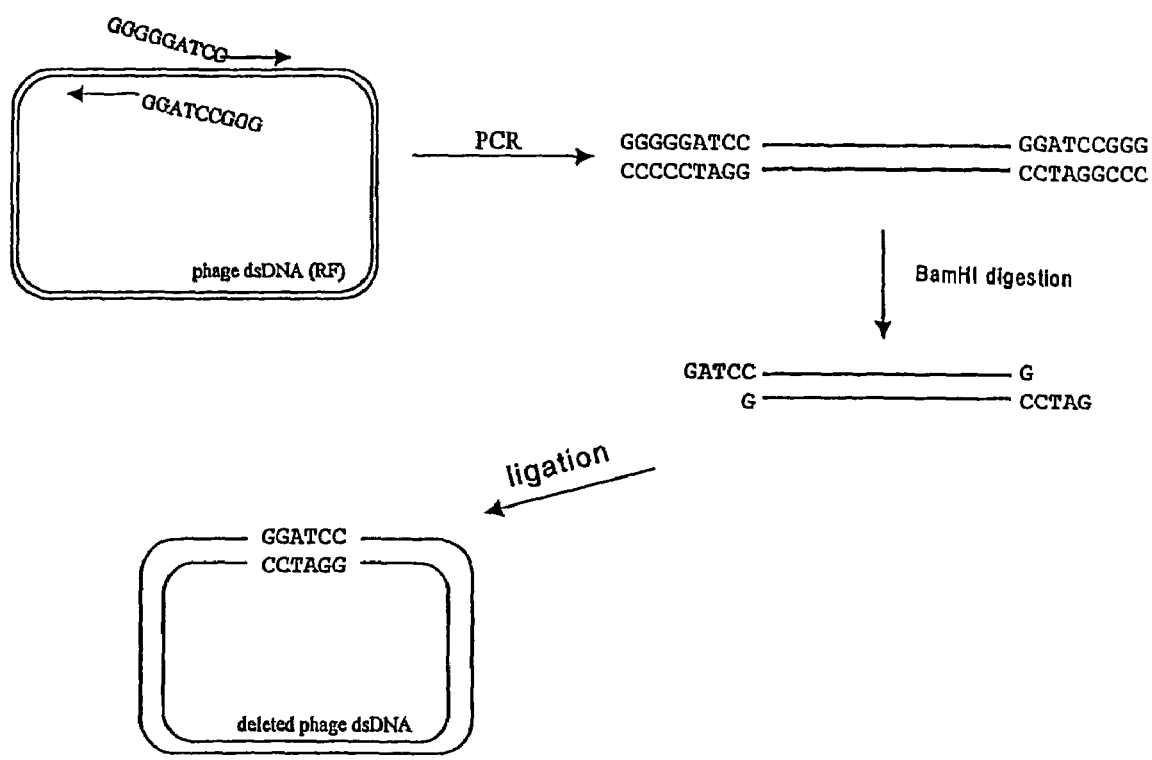

FIG. 10 is a picture showing a pattern diagram of the method for preparing deletion mutant by PCR method.

Figure 11:
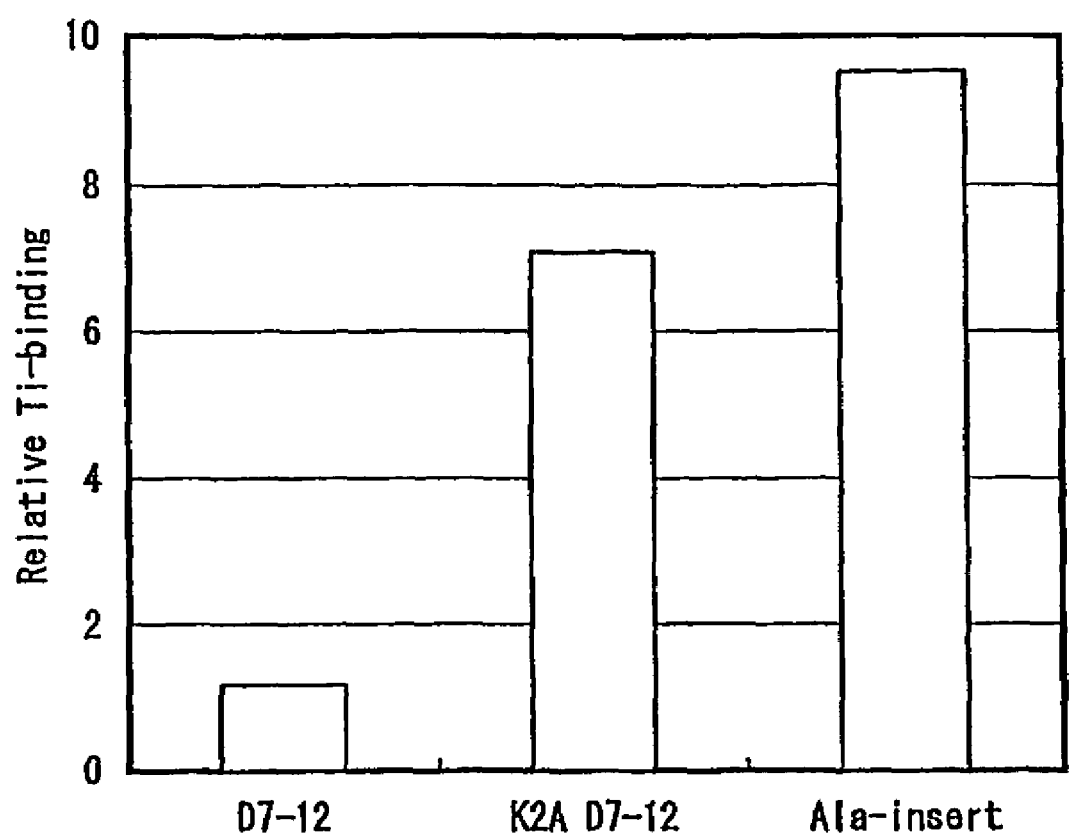

FIG. 11 is a picture showing the examination result of the influence of the deletion mutation and insert mutation on the binding ability of phage clone expressing a peptide shown in SEQ ID NOs: 2 to 15 to titanium.

The vertical axis represents the value of binding ability of point mutant, by fixing the binding ability of phage clone expressing a peptide shown in SEQ ID NO: 1 to 1; the horizontal axis represent deletion and insert mutants.

Figure 12:
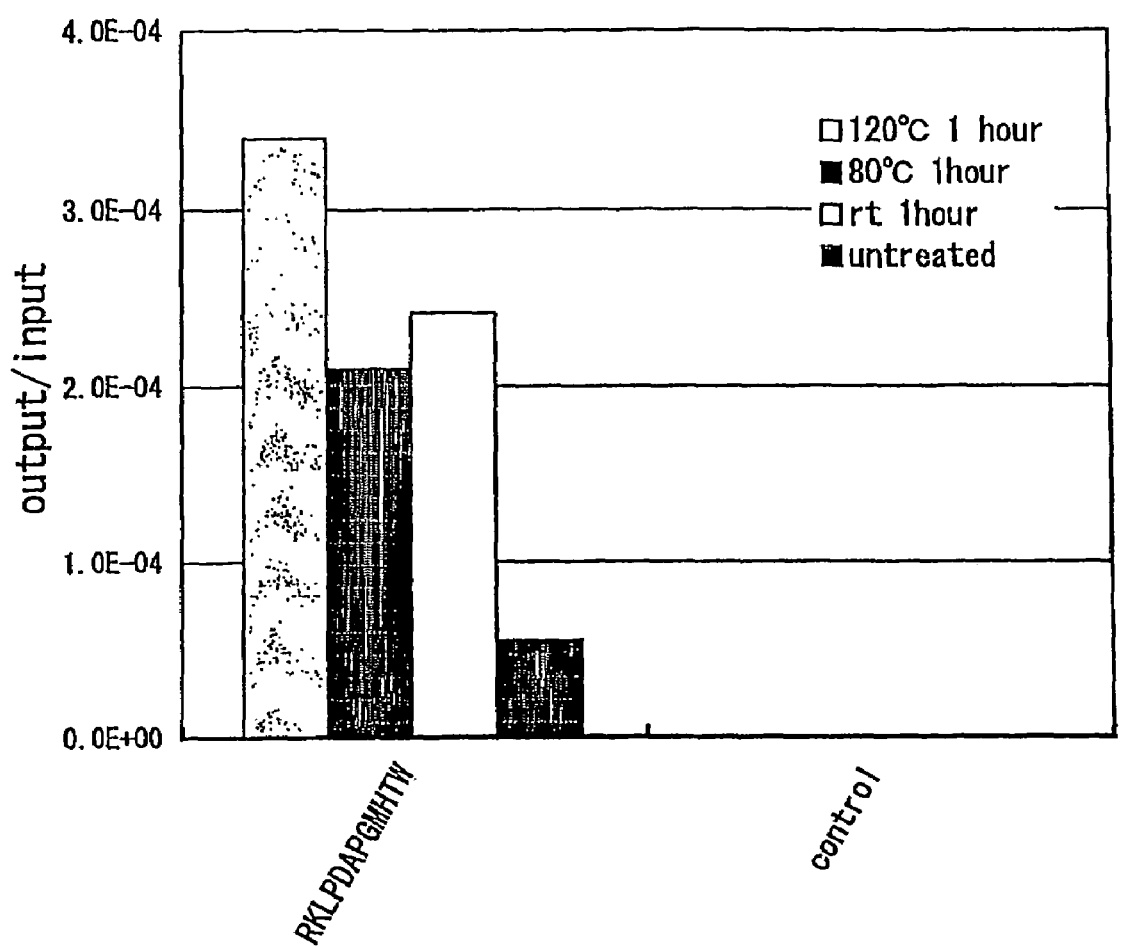

FIG. 12 is a picture showing the result of the influence of treating titanium particles with hydrogen peroxide, on phage binding ability.

Figure 13:
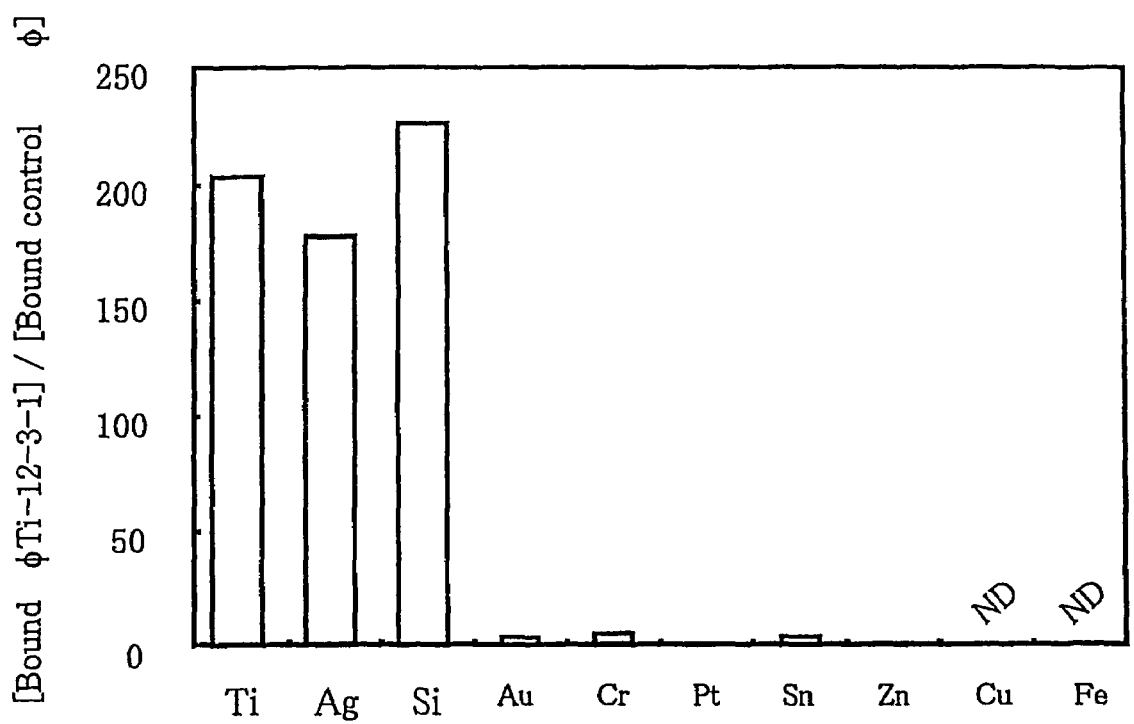

FIG. 13 is a picture showing the examination result of the binding ability of phage expressing a peptide comprising an amino acid sequence shown in SEQ ID: 3 to, various metals.

The vertical axis represents the value of the binding level of phage expressing a peptide comprising an amino acid sequence shown in SEQ ID NO: 3 divided by the binding level of phage without expressing sequence, showing the contribution of the binding by a peptide comprising an amino acid sequence shown in SEQ ID NO: 3. As for copper and steel, the binding level of both phages was below the detection limit.

Figure 14:
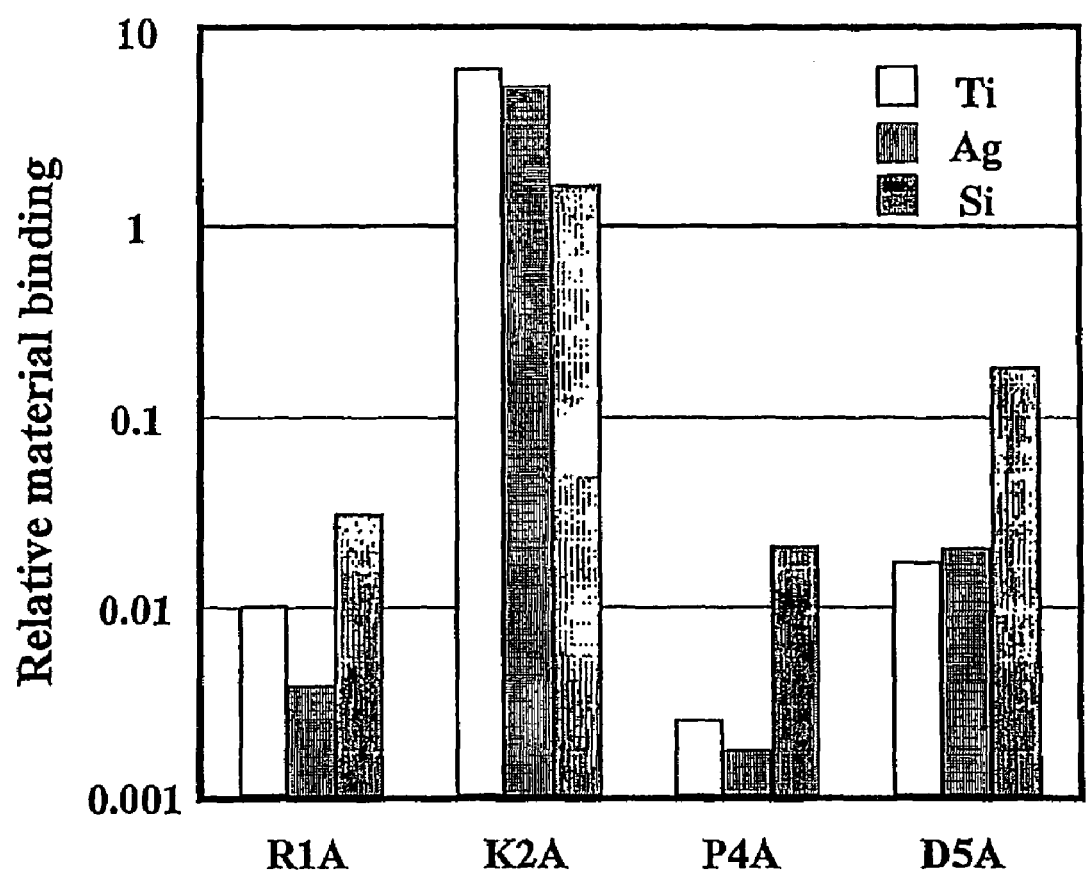

FIG. 14 is a picture showing the examination result of the influence of substitution mutation by alanine in the peptide comprising an amino acid sequence shown in SEQ ID NO: 3 on binding to titanium, silver, and silicon.

The vertical axis represents the standardized value by fixing the binding level of the phage expressing a peptide comprising an amino acid sequence shown in SEQ ID NO: 3 to 1.

Figure 15:
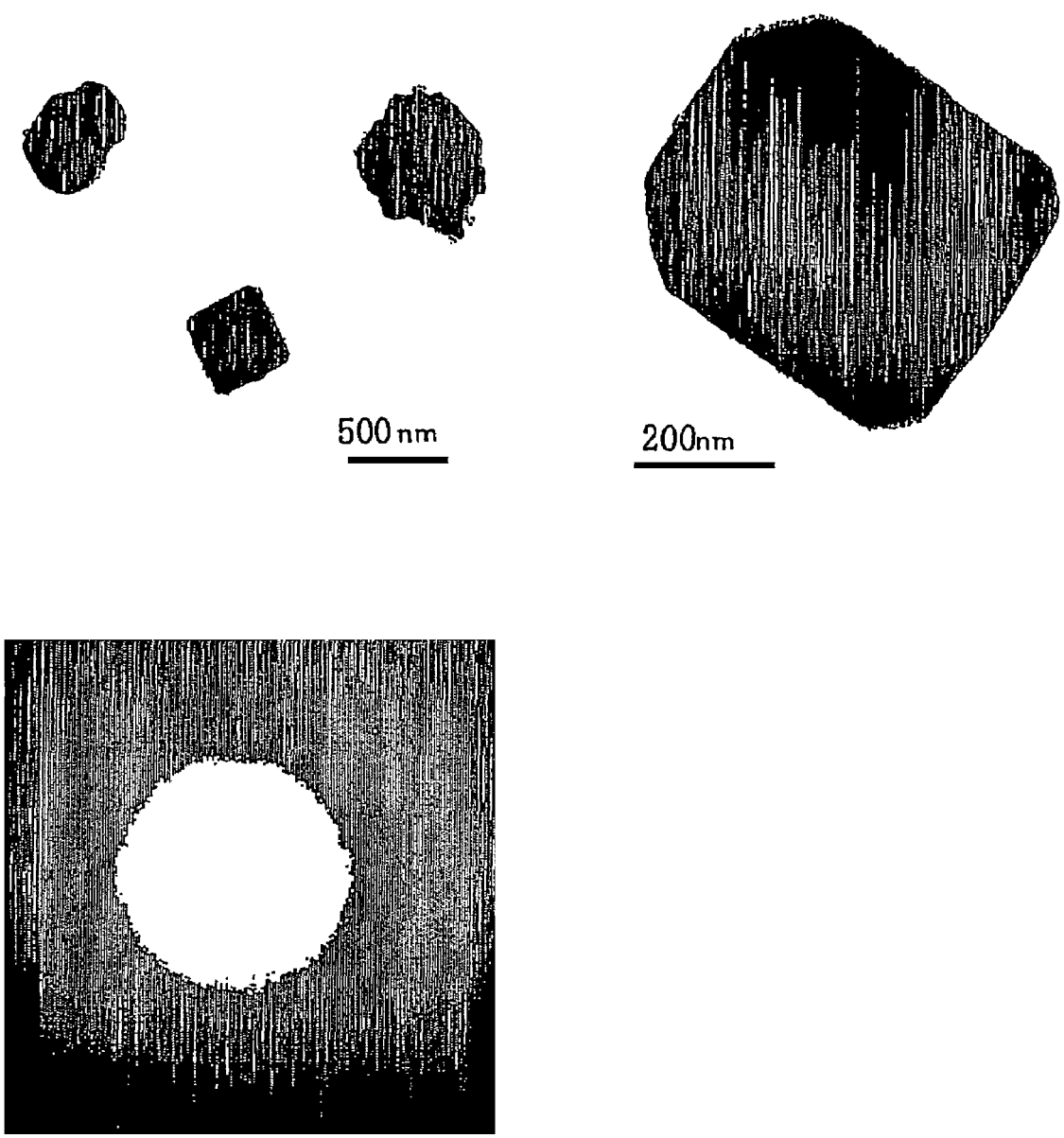

FIG. 15 is a picture showing the electron microscope image and electron diffraction pattern of a silver particle generated by biomineralization of the synthesized peptide comprising an amino acid sequence shown in SEQ ID NO: 3.

Figure 16:
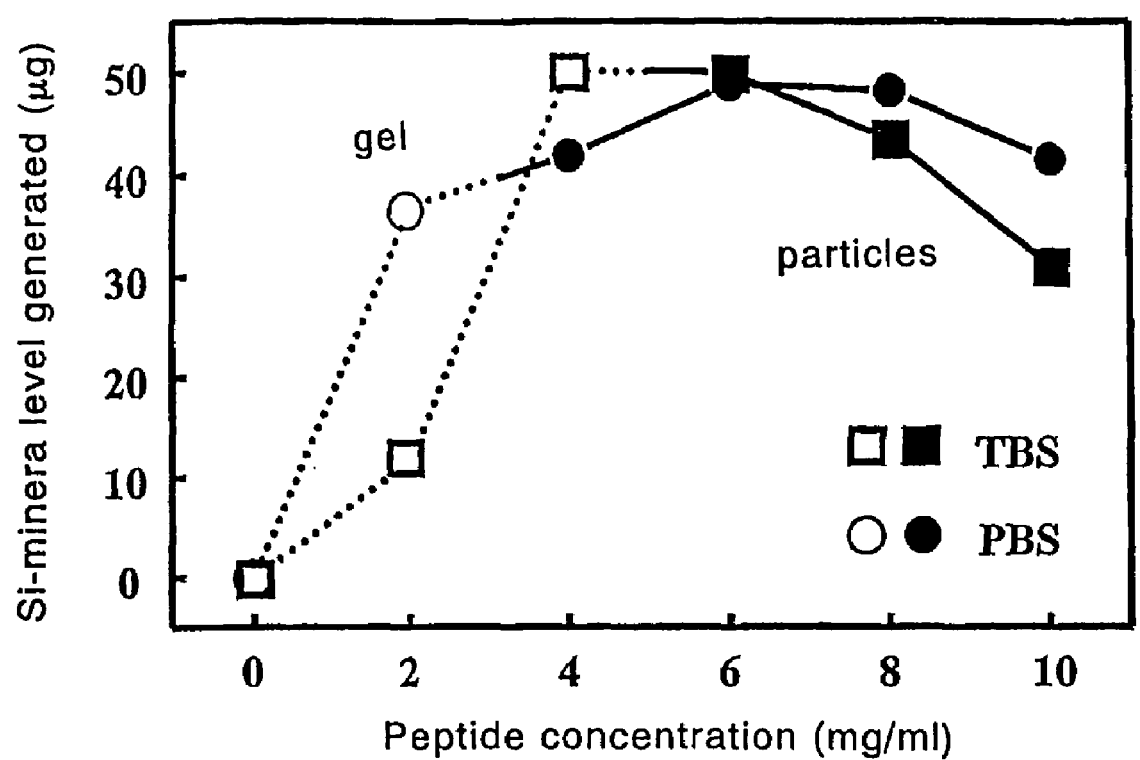

FIG. 16 is a picture showing the relation between the peptide concentration and the silica level generated by biomineralization of the synthetic peptide comprising an amino acid sequence shown in SEQ ID NO: 3.

Under the peptide concentration condition shown in white marks and dotted line, silica is formed in the form of gel. Under the peptide concentration condition shown in black marks and full line, silica is formed in the form of particles.

Figure 17:
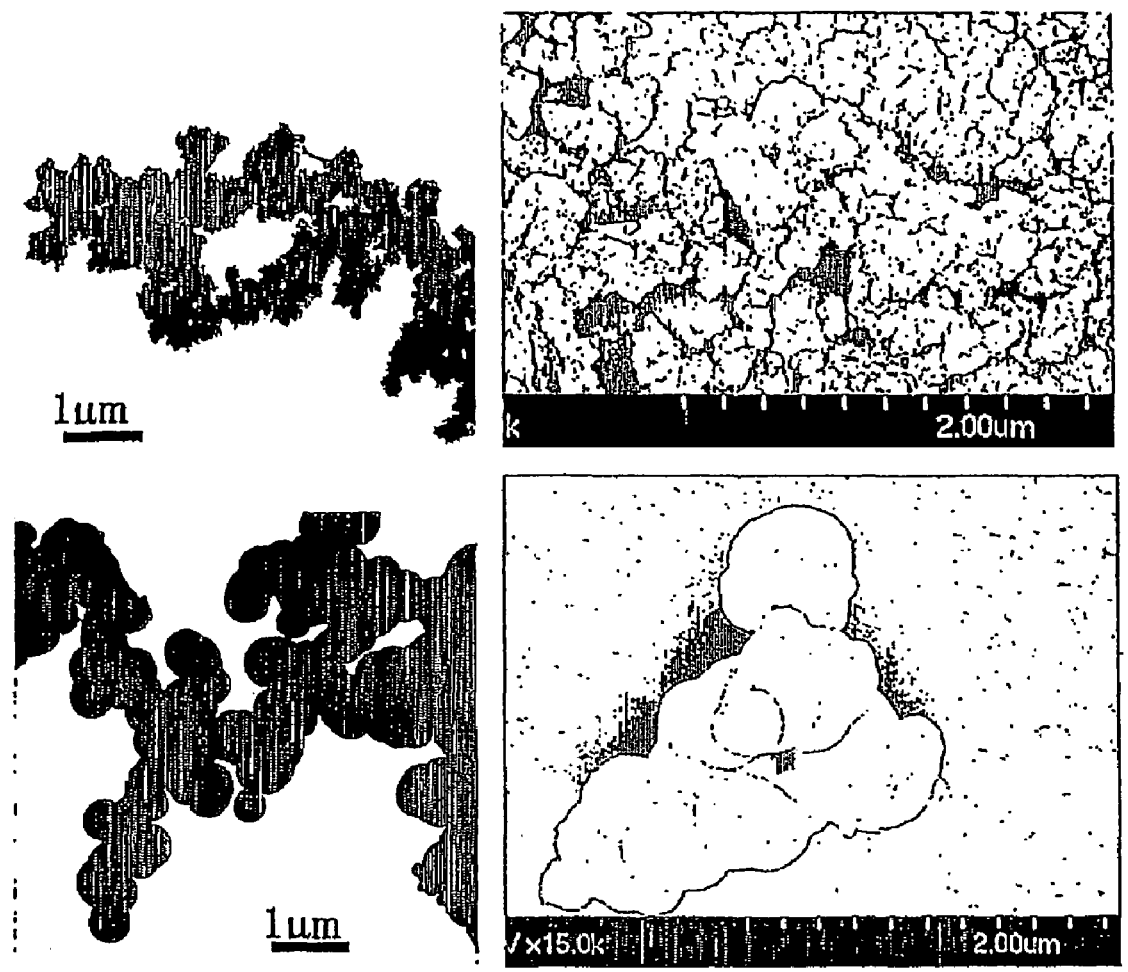

FIG. 17 is a picture showing a transmission electron microscope image and scanning electron microscope image of silica particles generated by biomineralization of the synthetic peptide comprising an amino acid sequence shown in SEQ ID NO: 3.

Figure 18:
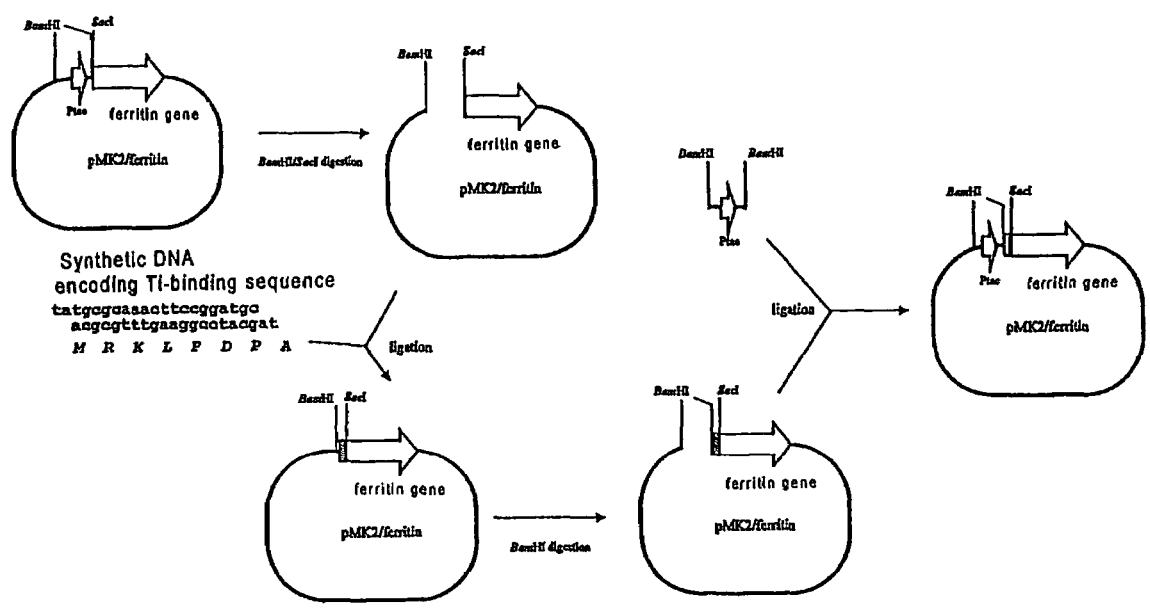

FIG. 18 is a picture showing a pattern diagram of the construction of a ferritin-expressing vector fusing a peptide comprising an amino acid sequence shown in SEQ ID NO: 1 Base sequence of the synthetic DNA encoding the Ti-binding sequence is shown in SEQ ID NO: 55 and base sequence of the synthetic DNA encoding polypeptide MRKLPDPA is shown in SEQ ID NO: 56.

Figure 19:
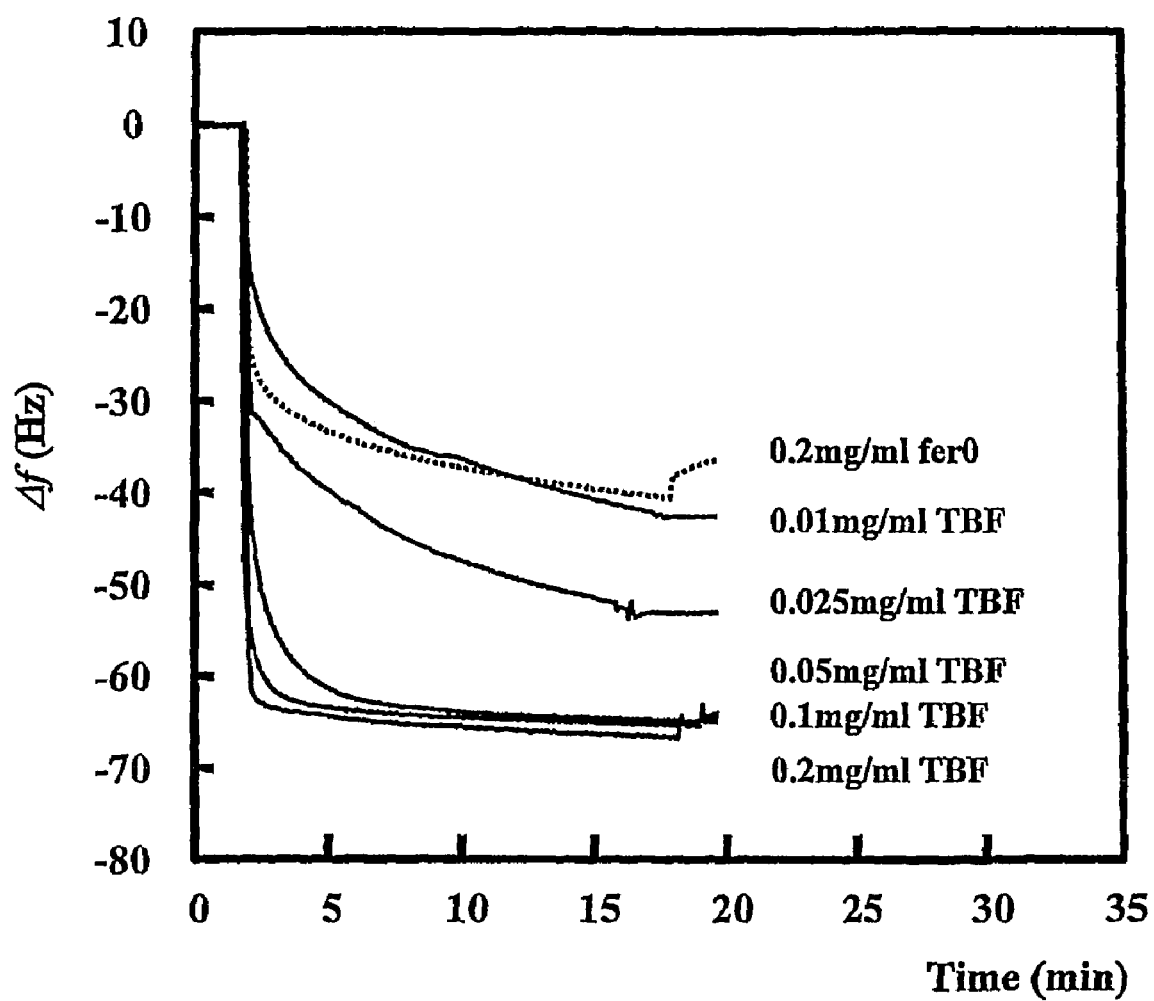

FIG. 19 is a picture showing a binding result of a recombinant ferritin fusing a peptide comprising an amino acid sequence shown in SEQ ID NO: 1 to titanium surface.

BEST MODE OF CARRYING OUT THE INVENTION

As for the method for screening a titanium binding peptide of the present invention, there is no particular limitation as long as it is a method for screening comprising the following steps:

contacting titanium with a population of phage (phage library) wherein said phage of said population collectively express (display) a library of different peptide sequence, preferably in an aqueous solution;

recovering titanium bound to phage particles via the peptide sequence by centrifugation;

proliferating the obtained titanium binding phage particles in bacteria such as *E. coli*; and next, repeating a panning operation comprising the contact of titanium with the proliferated titanium binding phage expressing a peptide sequence on phage particles and concentrating proliferating titanium binding phage clones. As for the above titanium, titanium such as titanium metal in form of particles, plates, etc., titanium alloy, titanium dioxide can be used. Further, the above mentioned phage library can be prepared as a phage expressing amino acid residue (-Xn-, X=any amino acid) of the random part to surface layer, by inserting a random DNA chemically synthesized to a phage DNA (phagemid), and transfecting to host *E. coli*, molecules forming phage virus are biosynthesized, and random peptides are expressed to the head of N terminal of coat protein pIII of viral particles. However, phage library that are commercially available (random 7 mer, 12 mer, cyclic 7 mer) can also be used.

As for the peptide having a binding ability to titanium, silver and/or silicon of the present invention, peptides having a binding ability to titanium, silver and/or silicon obtained by the method for screening a titanium binding peptide of the present invention mentioned above, or mutant thereof, can be exemplified. Specifically, a peptide (Δ7-12) having a binding ability to titanium, silver and silicon comprising the amino acid sequence RKLPDA shown in SEQ ID NO: 1, or a peptide (Δ7-12 mutant) having a binding ability to titanium, silver and/or silicon, comprising an amino acid sequence shown in SEQ ID NO: 1, wherein at least one amino acid is deleted, substituted, or added in the amino acid sequence can be exemplified preferably as having an excellent binding ability to titanium, silver and/or silicon. Among the above Δ7-12 mutant, a peptide wherein the 1st (Arg), 4th (Pro), 5th (Asp)

amino acid residue of the amino acid sequence shown in SEQ ID NO: 1 is conserved is preferable, and a peptide (K2A-Δ7-12) comprising an amino acid sequence shown in SEQ ID NO: 2 wherein the 2nd (Lys) is substituted by Ala is particularly preferable, as having an excellent binding ability to titanium, silver and silicon.

As for the peptide having a binding ability to titanium, silver and/or silicon of the present invention, a titanium binding peptide (e3-2-3) comprising the amino acid sequence RKLPDAPGMHTW shown in SEQ ID NO: 3; or a peptide (e3-2-3 mutant) having a binding ability to titanium, silver and/or silicon, comprising an amino acid sequence shown in SEQ ID NO:3, wherein at least one amino acid is deleted, substituted or added in the amino acid sequence can be preferably exemplified as having an excellent binding ability to titanium, silver and/or silicon. As for the above e3-2-3 mutant, peptides comprising an amino acid sequence shown in SEQ ID NOs: 4 to 14, wherein 1 to 5th and 7 to 12th amino acid residues are substituted by Ala, respectively (R1A, K2A, L3A, P4A, D5A, P7A, G8A, M9A, H10A, T11A, W12A); or peptides (Ala insert) comprising an amino acid sequence shown in SEQ ID NO:15 wherein Ala is added/inserted to N terminal of e-3-2-3 can be exemplified. Ala insert is particularly preferable as having an excellent binding ability to titanium, silver and/or silicon.

Further, as for the titanium binding peptide of the present invention, a peptide comprising an amino acid sequence shown in SEQ ID NOs: 16 to 24 derived from D12 library (New England Biolabs, Beverly) expressing linear random peptide of 12 residues; or a titanium binding peptide comprising an amino acid sequence shown in SEQ ID NOs:16 to 24, wherein at least one amino acid is deleted, substituted, or added in the amino acid sequence, can be exemplified, similarly to e3-2-3.

Moreover, as for the titanium binding peptide of the present invention, a peptide comprising an amino acid sequence shown in SEQ ID NOs: 25 to 38 derived from C7C library (New England Biolabs) expressing cyclic random peptide of 7 residues; or a titanium binding peptide, comprising an amino acid sequence shown in SEQ ID NOs: 25 to 38, wherein at least one amino acid is deleted, substituted, or added in the amino acid sequence, can be exemplified.

As for the level of "substitution, deletion or addition" of an amino acid or sites thereof, all of the modified peptides are encompassed in the present invention as long as they have a binding ability to titanium, silver and/or silicon, similarly to the peptides comprising an amino acid sequence shown in SEQ ID NO: 1 or 3.

Furthermore, titanium includes metal titanium, titanium alloy, amorphous titanium dioxide, titanium dioxide anatase crystal, titanium dioxide rutile crystal and titanium dioxide brookite crystal.

The above-mentioned titanium binding peptide group of the present invention (herein after these peptides will be referred to as "the present titanium binding peptide"), the silver binding peptide group (herein after these peptides will be referred as "the present silver binding peptide"), the silicon binding peptide group (herein after these peptides will be referred to as "the present silicon binding peptide") can be prepared by a general chemical synthesis method according to its amino acid sequence. Furthermore, the chemical synthesis method includes common peptide synthesis method by liquid phase method and solid phase method. The peptide synthesis method includes, more specifically, step-wise elongation method wherein each amino acid is bound one by one subsequently to elongate the chain according to the amino acid sequence information, and fragment condensation method wherein a fragment comprising a few amino acids is synthesized previously and that each fragment are brought to coupling reaction. The peptide synthesis of the present invention can be performed by any of these methods.

The condensation method applied to the above peptide synthesis can be performed according to various known methods. Specific examples include azide method, mixed acid anhydride method, DCC method, active ester method, redox method, DPPA (diphenylphosphoryl azide) method, DCC+additives (1-hydroxybenzotriazol, N-hydroxysuccinamide, N-hydroxy-5-norbornene-2,3-dicarboxyimide, etc.) and Woodward method. Solvents that can be used to these methods can be selected from common ones that are well known to be used in this type of peptide condensation method. Examples include dimethylformamide (DMF), dimethyl sulfoxide (DMSO), hexaphosphoroamide, dioxane, tetrahydrofuran (THF), ethyl acetate, etc. and mixed solvents thereof.

In the above peptide synthesis reaction, carboxyl group in amino acid or peptide that are not associated with the reaction, can be protected in general by esterification, for example by lower alkyl ester such as methyl ester, ethyl ester, tertiary butyl ester and the like, for example benzyl ester, p-methoxybenzylester, p-nitro-benzylester aralkyl ester and the like. Furthermore, amino acid having a functional group in its side chain, for example hydroxy group of Tyr can be protected by acetyl group, benzyl group, benzyloxycarbonyl group, tertiary butyl group, etc. However, such protection is not always necessary. Furthermore, for example guanidino group of Arg can be protected by an appropriate protection group such as nitro group, tosyl group, 2-methoxy benzene sulfonyl group, methylene-2-sulfonyl group, benzyloxycarbonyl group, isobornyl oxycarbonyl group, adamantyloxycarbonyl group, etc. Deprotection reaction of these protection groups in amino acid, peptide having the above protection group and the present titanium binding peptide finally obtained, can be performed by common methods, for example catalytic reduction method, or method using liquid ammonia/sodium, hydrofluoric acid, hydrogen bromide, hydrochloric acid, trifluoro acetate, acetic acid, formic acid, methanesulfonic acid, etc.

Moreover, the present titanium binding peptide and the like can be prepared according to common methods with genetic engineering technique, with the basic sequence information of DNA encoding the present titanium binding peptide and the like. Purification of the present titanium binding peptide thus obtained can be appropriately performed according to general methods, for example, methods commonly used in the field of peptide chemistry, such as ion exchange resin, partition chromatography, gel chromatography, affinity chromatography, high-performance liquid chromatography (HPLC), counter-current partition method, etc.

Additionally, chemically modified peptides can be used advantageously as the present titanium binding peptide, the present silver binding peptide and the silicon binding peptide. As for the chemical modification, chemical modification comprising substitution to amino acid having a functional group, or chemical modification in order to form easily the binding with linker can be exemplified. However, modification that does not decrease the binding ability to titanium, silver and silicon is preferable. For example, as for the above-mentioned chemical modification in order to form easily the binding with liker, covalent binding of biotin to amino group of peptide by using N-hydroxysuccinimide ester compound of biotin can be exemplified. By the biotinylation of peptides, chimeric molecules described in the following can be easily prepared.

As for the artificial protein having a binding ability to titanium, silver and silicon of the present invention, there is no specific limitation as long as it comprises a conjugate of the present titanium binding peptide, the present silver binding peptide, the silicon binding peptide with a functional peptide or a functional protein. As for the function of the above functional peptide or protein, the following functions can be exemplified: function for forming easily secondary structure such as α-helix, function promoting calcification, function inducing bone growth/differentiation, chromophore-binding function, collagen-binding function, cell adhesion function, function to localize protein extracellularly, function for targeting particular intracellular organelles (mitochondria, chloroplast, ER, etc.), function to be embedded to cell membrane, function for forming amyloid fiber, function for forming fibrous protein, function for forming protein gel, function for forming protein film, function for forming monolayer, self-assembly function such as forming two-dimensional crystals by self-assembly, function for forming particles, function to assist conformational formation of other proteins, antigen function inducing neutralizing antibody such as virus, and immunostimulating function (Nature Medicine, 3: 1266-1270, 1997); function promoting or suppressing cell proliferation, function for recognizing specifically cancer cells, protein-transduction function, function inducing cell death, function expressing antigen-determining residue, metal binding function, coenzyme binding function, catalyst activating function, fluorescence coloring-activating function, function for binding to a particular receptor and activating the receptor, function for binding to a particular factor related to signaling and modulating the function, and function for recognizing specifically biopolymers such as protein, DNA, RNA, sugar, etc. These artificial proteins can be prepared by binding directly or indirectly a functional peptide or a functional protein to a peptide having a binding ability to titanium at the amino acid level or at the DNA level. When preparing at the DNA level, engineering technology for artificial proteins disclosed in "Method for preparing high molecular microgene polymer" (Japanese Patent No. 3415995) or "Multifunctional base sequence and artificial gene including thereof" (Japanese Laid-Open Patent Application No. 2001-352990), disclosed by the present inventors.

Among the above functional peptides or functional proteins, by using a peptide or a protein that can form a two-dimensional crystal by self-assembly by cooperating with a peptide having a binding ability to titanium, silver or silicon, for example, it is possible to construct an artificial protein that can align titanium, silver or silicon along the two-dimensional crystal orderly at a nano scale. As for a peptide or a protein that can form a two-dimensional crystal by self-assembly by cooperating with a peptide having a binding ability to titanium, silver or silicon, examples include virus (for example, adenovirus, rotavirus, poliovirus, HK97, CCMV, etc.), ferritin family such as ferritin or apoferritin, DpsA protein or MrgA protein. As for other peptides or proteins that can form a two-dimensional crystal by self-assembly, artificial proteins with enhanced repeatability, designed artificially can be exemplified. Furthermore, as for a method for preparing a two-dimensional crystal of protein, a method comprising the steps of developing protein solution on water surface with monolayer, and adsorbing on a solid plate, can be exemplified.

Moreover, among the above functional peptide or functional protein, for example by using a peptide or a protein comprising a peptide sequence having a cell-recognizing activity such as cell adhesion activity, an artificial protein with conjugated activity to recognize titanium, silver or silicon, and cells simultaneously can be obtained. As for the peptide or protein comprising a peptide sequence having a cell-recognizing activity such as cell adhesion activity, examples include various ligands, monoclonal antibodies or variable region thereof, single-strand antibody etc., and moreover, artificial proteins comprising a peptide having cell adhesion activity, not limited to natural proteins, as mentioned above.

As for the chimeric protein having a binding ability to titanium, silver or silicon of the present invention, chimeric molecules comprising a conjugate of the present titanium binding peptide, the present silver binding peptide, or the present silicon binding peptide, with a labeled substance that can provide signal detectable separately or by reacting with other materials, or a peptide tag can be exemplified. As for the above labeled substance, enzyme, fluorescent substance, chemical luminescent substance, radioisotope, Fc region of antibodies, etc. can be exemplified. Specifically, examples include: enzyme including peroxidase (for example, horseradish peroxidase), alkaline phosphatase, β-D-galactosidase, glucose oxidase, glucose-6-phosphate dehydrogenase, alcohol dehydrogenase, malate dehydrogenase, penicillinase, catalase, apoglucose oxydase, urease, luciferase or acetylcholine esterase; fluorescent substances including fluorescein isothiocyanate, phycobiliprotein, rare-earth metal chelate, dansyl chloride or tetramethylrhodamine isothiocyanate, etc.; radioisotopes including $^3$H, $^{14}$C, $^{125}$I, etc.; and chemical luminescent substance. Further, as for peptide tags, conventionally known peptide tags including epitope tag such as HA, FLAG, Myc; or affinity tag such as GST, maltose-binding protein, biotinylated peptide, oligohistidin (His) can be specifically exemplified. For example, by using the affinity of His tag and Ni-NTA, titanium/peptide or protein complex can be easily purified.

As for the chimeric protein having a binding ability to titanium, silver or silicon of the present invention, chimeric molecules comprising a conjugate of the present titanium binding peptide, the present silver binding peptide, or the present silicon binding peptide, with nonpeptide compounds can be exemplified. Among the above non-peptide compounds, as for nonpeptide low molecular compounds, fluorochrome such as fluorescein and rhodamine, antibiotics such as chloramphenicol and ampicillin can be specifically exemplified. Moreover, as for nonpeptide high molecular compounds, polystyrene, polypropylene, polyethylene, glass bead, silicagel, polysaccharides (including derivatives), polyalkylene glycol such as polyethylene glycol can be specifically exemplified.

As for the phage having a binding ability to titanium, silver or silicon of the present invention, there is no particular limitation as long as it is a phage expressing the present titanium binding peptide, the present silver binding peptide, or the present silicon binding peptide on the particle surface. Moreover, as for the phages having a binding ability to titanium, silver or silicon, it can be obtained as phage clones binding to titanium, silver or silicon, by separating the peptide-expressing phage strongly bound to titanium molecule, silver molecule or silicon molecule from other phage groups during the above-mentioned screening process. Further, it can be also obtained by integrating DNA encoding the present titanium binding peptide, the present silver binding peptide or the present silicon binding peptide to a phagemid vector to transfect host cells such as *E. coli* and infecting helper phage. In general, filamentous phages such as M13 or fd take a liquid crystal state in a high-concentration state, and take a regular alignment construction. Therefore, by making a liquid crystal state of the peptide phage recognizing titanium, a condition wherein peptides recognizing titanium, are aligned regularly in a nano scale can be obtained. By bringing titanium into contact, it is possible to align titanium with the titanium-recognizing ability of the peptides.

As for the complex of titanium, silver or silicon with a peptide, the complex of titanium, silver or silicon with an artificial protein, the complex of titanium, silver or silicon with a chimeric protein, the complex of titanium, silver or silicon with a phage of the present invention, examples include a complex wherein the above-mentioned peptide having a binding ability to titanium, silver or/and silicon, the above-mentioned artificial protein having a binding ability to titanium, silver and/or silicon, the above-mentioned chimeric protein having a binding ability to titanium, silver and/or silicon, or the above-mentioned phage having a binding ability to titanium, silver and/or silicon is bound with titanium, silver or silicon by any weak bindings such as ion binding, $\pi$ electronic binding, van der Waals binding, hydrophobic binding, etc. or combination thereof. Particularly, titanium-artificial protein complex can be used advantageously as implant material, photocatalyst, pigment, etc.

By using cytokines promoting bone differentiation fusing a titanium binding peptide, for example those binding BMP to titanium implant material via a titanium binding peptide, aggressive bone formation occurs nearby titanium implant. Thus, it can be expected that the duration of osseointegration can be shortened. Further, by using as a peptide or a protein promoting biomineralization of hydroxyapatite fusing artificially a titanium binding peptide, those bound to titanium implant material via a titanium binding peptide, calcification of the titanium implant surface is promoted and thus, it can be expected that the duration of osseointegration can be shortened. Alternatively, by using as a peptide or a protein or a compound having an antibacterial activity fusing artificially a titanium binding peptide, those bound to titanium implant material via a titanium binding peptide, infectious diseases during osseointegration can be decreased. Moreover, by binding collagen fusing a titanium binding peptide to titanium implant material via a titanium binding peptide, it is possible to construct a construction that could not be observed in conventional artificial dental root, just as collagen fiber were bound perpendicularly to artificial dental root. This is imitating a mechanism dispersing the force that teeth have originally when a strong force is applied, and thus, when a strong force is applied to an artificial dental root, a higher stability can be obtained compared to conventional artificial dental root.

As the titanium binding peptide can be bound to silver simultaneously, for example, cosmetics wherein collagen fusing a titanium binding peptide is bound to oxidized titanium pigment and silver, can have a high antibacterial activity.

According to the method for refinement of a titanium surface using the present titanium binding peptide of the present invention, to the method for refinement of a titanium surface for forming a titanium particle, or for aligning titanium, using the artificial protein of the present invention bound to the present titanium binding peptide, to the method for refinement of titanium surface or for forming a titanium particle using the chimeric protein of the present invention bound to the present titanium binding peptide, or to the method for aligning titanium or for forming a titanium particle by using the phage of the present invention expressing the present titanium binding peptide on the particle surface, it is possible to improve the characteristic of titanium surface or the physical property of titanium, and particularly, the development of device at a nano scale would be possible with the patterning of oxidized titanium by using the self-assembly ability of protein.

Furthermore, according to the method for refinement of a silicon surface or a silver surface, or for forming a silver particle or a silicon particle, using the present silver binding peptide or the present silicon binding peptide, or to the method for refinement of a silicon surface or a silver surface, or for forming a silver particle or a silicon particle, or for aligning silver or silicon, by using the artificial protein of the present invention bound with the present silver binding peptide or the present silicon binding peptide, or to the method for refinement of a silver surface or a silicon surface, or for forming a silver particle or a silicon particle, by using the chimeric protein of the present invention bound with the present silver binding peptide or the present silicon binding peptide, or to the method for forming a silver particle or a silicon particle or for aligning silver or silicon, by using the phage of the present invention expressing the present silver binding peptide or the present silicon binding peptide on the particle surface, it is possible to improve characteristics of silver surface or silicon surface or the physical properties of silver/silicon.

In particular, by refinement of a titanium surface, a silver surface, or a silicon surface, it is possible to confer biomineralization ability that forms minerals (inorganic compounds) inside and outside of the living organism itself.

Further, by using the present titanium binding peptide, the present silver binding peptide, or the present silicon binding peptide as a probe of atomic force microscope (AFM), it is possible to perform analysis of solid material surface in an aqueous solution. For example, the present titanium binding peptide, or an artificial protein/chimeric protein fusing titanium binding peptide is fixed to the probe of atomic force microscope by for example gold/thiol binding. By approaching the probe to the substrate of titanium/silver/silicon, an interaction is generated between the titanium binding peptide and the substrate and the interaction is disrupted by separating the probe. The tension thus generated can be measured. Further, by scanning the probe two-dimensionally, a force map having the binding force of the surface of substrate and the titanium binding peptide as an index can be made. According to the force map made, it is possible to select in a wide variety materials and crystal surface that is appropriate to patterning.

In the following, the present invention will be explained in detail, with reference to the examples, but the technical scope of the present invention is not limited to these examples.

EXAMPLE 1

10 mg of titanium particle with a particle diameter of 150 µM (Sumitomo Titanium Corporation, Hyogo) was put into a 1.5 ml-Eppendorf tube, and washed twice with a solution of 500 µl of 50 mM tris (hydroxymethyl) aminomethane (herein after referred to as tris (Kishida Chemical (Osaka)) HCl buffer pH 7.5; 150 mM of sodium chloride (Wako Pure Chemicals, Osaka) solution (herein after referred to as TBS) supplemented with 0.1% bovine serum albumin (herein after referred to as BSA), 0.1% Polyoxyethylenesorbitan monolaurate (herein after referred as Tween-20 (Sigma, St. Louis)). Washing of titanium particles was performed by centrifuging with a desktop centrifuge H1300 (Kokusan) at 13,000 rpm, 5 sec, to precipitate titanium particles and to remove supernatant. After washing, in order to block the non-specific adsorption of the phage, the mixture was stirred by rotating with 1 ml of the same solution for 30 min at room temperature by using a rotary shaker rotator RT-50 (Taitec).

By centrifuging with a desktop centrifuge H1300 (Kokusan) at 13,000 rpm, 5 sec, titanium particles were precipitated, the supernatant was removed, and then 1 ml TBS containing peptide-expressing phage library, D12 library expressing linear random peptide of 12 residues (New England Biolabs, Beverly), $17 \times 10^{11}$ plaque-forming unit (herein after referred to as pfu), or C7C library expressing cyclic randam peptide of 7 residues (New Engand Biolabs) $2.0 \times 10^{11}$ pfu, 0.1% BSA and 0.1% Tween-20 solution were added, and stirred by rotating for 2 hours, at room temperature with a rotary shaker, rotator RT-50.

By centrifuging with a desktop centrifuge H1300 (Kokusan) at 13,000 rpm, 5 sec, the supernatant was removed, and the resultant was washed 10 times with 1 ml of TBS, 0.1% Tween-20 solution. Washing was performed by centrifuging at 8000×g, 5 sec, by precipitating titanium particles. After removing washing solution, 1 ml of 0.2 M glycine (Wako Pure Chemicals), HCl buffer pH 2.2 were added and stirred by rotating for 10 min at room temperature with rotator RT-50 (Taitec) to elute phage bound to titanium. Titanium was precipitated by centrifugation, and the supernatant was moved to a separate 1.5 ml-Eppendorf tube. Then, 150 µl of 1M tris/HCl buffer pH 9.1 was added to neutralize, and phage titer in the solution (plaque forming ability per unit solution) was measured according to a common procedure (Molecular Cloning Third Edition, Cold Spring Harbor Laboratory Press).

Phage eluate obtained by the above operation, was infected to *E. Coli* ER2738 strain [F'lacI$^q$Δ(lacZ)M15proA$^+$B$^+$zzf::Tn10(TetT)fhuA2 supE thiΔ(lac-proAB)Δ(hsdMS-mcrB)5 ($r_k^-m_k^-$McrBC$^-$)] in logarithmic growth phase in 20 ml LB medium, stirred aggressively at 37° C. with a shaking incubator (BR-40 LF, Taitec) and incubated for 6 hours. Phage-infected culture solution was moved into a centrifuge tube (50 ml, Beckman, Calif.), and with a Beckman centrifuge (Beckman, JA-12 roter), the resultant was centrifuged twice at 4° C., 10 min, at 10,000 rpm, and the operation to remove ER2738 strain was performed twice. Then, the phage solution of the supernatant was moved to another tube. To the phage solution, 3.5 ml (⅙ amount) of 20% Polyethylene glycol 6000 (herein after referred to as PEG6000, Fluka, Bucks), 2.5 M NaCl solution was added. The mixture was stirred well with a test tube mixer TM252 (Iwaki), and incubated at 4° C. for 12 hours, to precipitate phages.

The precipitated phages were centrifuged with a Beckman centrifuge at 4° C., for 10 min, at 10,000 rpm and recovered. Phage precipitates were further centrifuged at 4000 rpm for 1 min, and the little remaining supernatant was completely removed. 1 ml TBS was added to the obtained phage precipitates, cooled on the ice and suspended gently the phages. The phage suspension was moved to a 1.5 ml-Eppendorf tube, centrifuged with a micro high-speed centrifuge (AT2018M Roter, Kubota) for 5 min, at 15,000 rpm. The supernatant was moved to a separated tube, and the non-suspended residues were removed. 200 µl of 20% PEG6000, 2.5 M NaCl solution were added again to the phage solution, and the mixture was well stirred with a mixer and incubated on ice for 1 hour, to precipitate phages. Next, the resultant was centrifuged with a micro high-speed centrifuge for 10 min, 15,000 rpm and collected the phage precipitants. To the obtained phage precipitates, 200 µl of 0.02% sodium azide (Wako Pure Chemicals, Osaka), TBS were added for complete suspension. The non-suspended residues were removed by centrifuging with a micro high-speed centrifuge for 5 min, at 15,000 rpm. Titer of the obtained concentrated phage solution was calculated.

A series of operation comprising binding of a phage to a target molecule (for this case, titanium), washing, harvesting, proliferation by *E. coli*, as mentioned in the above, is called a panning operation. By repeating panning operation, it is possible to concentrate phage clone binding strongly specifically to a target molecule. In this case, after the first panning operation, second and following panning operations including binding to titanium, washing, harvesting and proliferation were repeated using phages once proliferated with *E. coli*. The following was different for the experimental condition for panning operation after the second time, compared to that of the 1st operation. In other words, the titer of phage to be added in the second and following panning operation, was prepared to be: $2.0 \times 10^{11}$ for both D12 library/C7 library for the 2nd time; $2.0 \times 10^{10}$ for both D12 library/C7C library for the 3rd time; $4.3 \times 10^9$ for D12 library and $2.0 \times 10^{10}$ for C7C library for the 4th time. Concentration of the solution in which the concentrated phage is suspended, reaction solution of titanium and Tween-20 in the washing solution was made to be 0.1%, 0.3% and 0.5% for the 2nd, 3rd, 4th panning operation, respectively.

Figure 1:
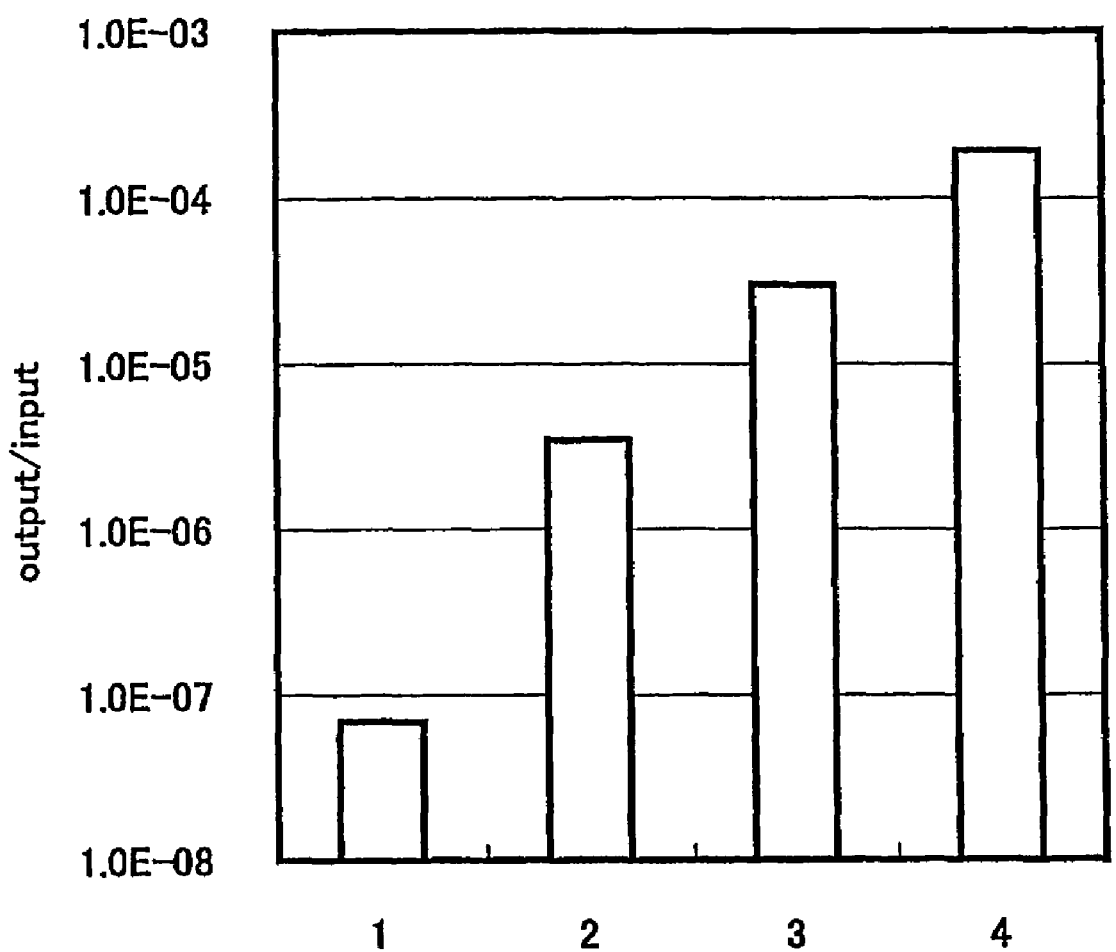
FIG. 1 is a picture showing the result of panning titanium particles by using D-12 phage library.

The change of ratio of the input titer (phage titer added to a target molecule) and the output titer (phage titer eluted from the target molecule after washing) of the panning experiment using D12 library is shown in FIG. 1. Moreover, the change of ratio of the input titer and output titer of the panning experiment in C7C library is shown in FIG. 2.

Phages obtained in the 3rd round in D12 library and C7C library were cloned according to a common procedure (Phage Display A Laboratory Manual, Cold Spring Harbor Laboratory Press, 2001) and the base sequence of the expressed peptide part was determined. The determination of base sequence was made by dideoxy termination method (CEC DTCS Quick start kit, Beckman, Calif.) by using a primer corresponding to a complementary chain of a base sequence located 96 bases downstream from the expressed peptide region [−96gIII sequencing primer (5'-$^{HO}$CCCTCATAGT-TAGCGTAACG-3') (SEQ ID NO: 39), NEB, Beverley]. For electrophoresis of the reaction products and data analysis, capillary auto-sequencer (CEQ2000, Beckman) was used.

The expressed peptide sequence estimated from the determined DNA sequences are shown in FIG. 3 for D12 library (SEQ ID NOs: 3, 16 to 24), and in FIG. 4 for C7C library (SEQ ID NOs: 25 to 38), respectively.

As for the peptide sequence expressing e3-2-3 phage obtained from D12 library, RKLPDAPGMHTW (SEQ ID NO: 3), among the 43 clones examined, there were 33 having the same sequence. One of the reasons why a particular phage clone becomes a majority in the group, is that the phage clone has a strong binding ability to the target molecule.

The phage expressing peptides shown in FIG. 3 (SEQ ID NOs: 3, 16 to 24) and FIG. 4 (SEQ ID NOs: 25 to 38) were cloned and the binding ability to titanium in a cloned condition was evaluated as follows.

EXAMPLE 2

By using the phage clone obtained in Example 1, the binding ability to titanium was evaluated by the following experiment. The same method as for panning operation shown in Example 1 was performed. The difference between Example 1 is that the stirring time of titanium and phage clone was 1 hour; the Tween 20 concentration and BSA concentration in each solution was 0.5%, and 1%, respectively, and that the titer of the phage added was $10^9$ pfu for clone from D12, and $10^{11}$ pfu for clone from C7C. The binding ability of titanium of each phage clone is shown in FIG. 5.

EXAMPLE 3

As for the clone strongly bound particularly with titanium (expressing peptide of SEQ ID NO: 3), the binding form of titanium surface and phage was examined, by measuring with QCM-D300 (Q-sense AB, Goeteborg), which is a device for quantification of interaction with a quartz crystal microbalance.

For a quartz crystal microbalance, titanium sensor being a genuine part of QCM-D300 was used. The temperature was fixed at 24.99° C., and the actual measurement value was from around 24.68° C. to 24.70° C. It was measured in a condition of blocking the sensor with BSA, and in a condition without blocking. When blocking with BSA is not performed, after measuring the standard value with TBS, the phage solution adjusted so that the phage titer becomes $10^{10}$ pfu/ml was measured continuously. When blocking with BSA is performed, after measuring the standard value with TBS, blocking was conducted by incubating for about 10 min with TBS, 0.1% BSA, and after washing again migrated BSA with TBS, the phage solution adjusted so that the phage titer becomes $10^{11}$ pfu/ml was measured continuously. The results are shown in FIG. 6.

From the results shown in FIG. 6, it is clear that the phage clone is bound to the sensor from the change of frequency, under the absence of BSA. However, as the viscoelasticity is not increased significantly, it is estimated that phage is strongly bound to titanium surface horizontally, as it is shown in FIG. 7 (bottom). On the other hand, when sensor is blocked with BSA, it can be seen that the phage amount binding to the sensor is small from the small change of the frequency, while the viscoelasticity is increased significantly. These results suggest that, as it is shown in FIG. 7 (upper), phage is bound to titanium surface mostly in the expressing peptide region, and that other phage particle parts exist in the solution, being not bound to titanium. However, as for control phage, non-specific adsorption to titanium surface under the absence of BSA is observed in the same manner, while the increase of viscoelasticity is not observed when it is blocked with BSA.

EXAMPLE 4

For clone strongly bound particularly with titanium (SEQ ID NO: 3) in Example 2, point mutants substituted by alanine having only one methyl group in the side chain was prepared and the change of binding ability to titanium was examined for each mutant phage. As point mutant comprises alanine in the 6th position in the expressed sequence, mutants were prepared for all the residues except the 6th residue. The preparation of point mutants was performed by Kunkel method (Molecular Cloning Third Edition, Cold Spring Harbor Laboratory Press). Synthetic DNAs used for preparing point mutants are shown in FIG. 8 (SEQ ID NOs: 40 to 50). The introduction of point mutation was confirmed by determining the DNA sequence of phage DNA. DNA sequencing was performed in the same manner as Example 1. The binding ability to titanium of the obtained point mutants was measured by the method shown in Example 2, by adjusting the phage amount added to $10^{10}$ pfu. The binding ability to titanium of each point mutant was shown in FIG. 9.

From the results shown in FIG. 9, it can be assumed that the charge of the side chain of 1st arginine, and 5th aspartic acid play an important role to the binding with titanium. Moreover, from the results of the mutant of 4th proline, it is suggested that the bending of the main chain of the peptide in 4th proline is very important.

EXAMPLE 5

From the results of Example 4, those important to the binding to titanium are concentrated in the amino-terminal part of SEQ ID NO: 3. Therefore, mutants wherein the 7 to 12th are deleted from the carboxyl-terminal side were prepared and the change of the binding ability to titanium was examined. Moreover, similar deletion mutant for mutant whose binding ability was increased in Example 4, wherein the 2nd lysine is substituted by alanine was prepared and the change of the binding ability to titanium was examined.

The deletion mutants were prepared by the method shown schematically in FIG. 10. Double stranded DNA of each phage clone (herein after referred to as RF) was prepared by using QIAGEN kit. PCR was performed by making the obtained RF as a matrix. To the primer used (FIG. 8, SEQ ID NOs: 51 to 53), poly G sequence of 3 residues was added to 5-terminal side so that cleavage with restriction enzyme BamHI cleavage site and BamHI is possible at 5'-terminal side. As for reagent, Expand™ Long Template PCR System (Boehringer) was used. Expand™ Long Template PCR System is composed of (1) an enzyme mix containing thermostable Taq DNA polymerase and Tgo DNA polymerase; and (2) a buffer. The reaction was performed with 100 μl solution comprising 1 μl polymerase, 10 μl 10× buffer solution 2 attached, 8 μl 2.5 mM dNTPs, 1 μl each of primer each 100 pmole/μl, and 0.5 μl RF. PCR reaction was performed for 30 cycles of 30 sec at 94 C, 30 sec at 60 C, 6 min at 72 C. Furthermore, before the cycle, 5 min-preheat was performed at 94 C, and after the cycle, the mixture was incubated for 7 mm at 72 C. After the PCR reaction, the product was separated by 1% agarose gel electrophoresis, and the band around 7 kb which is of the intended size was cut off under UV, and by using Geneclean II kit (Funakoshi), the band was purified according to the attached protocol. The purified DNA was incubated at 30 C for 2 hours with restriction enzyme BamHI (Boehringer). Then, BamUl was inactivated by ethanol precipitation to dry DNA. The dried DNA was dissolved into 4 μl of sterile water and 5 μl of 2× ligation buffer (Promega). Then, 1 μl of T4 DNA ligase (Roche) was added, ligation reaction was performed at room temperature for 30 min for self-ring closure. To the reaction solution, 100 μl of competent cells of *E. coli* ER2738 strain described in Example 1 was added, the mixture was left stand on ice for 30 min, and after adding heat shock of 42 C for 40 sec was put immediately on ice for 3 min. Then, 800 μl of SOC medium was added, cultured by shaking aggressively for 3 hours at 37 C. Then, 1, 10, 100 μl was mixed with 200 μl of ER2738 strain in logarithmic growth phase, and left stand for 5 min Afterwards, the resultant was cloned according to a common procedure (Molecular Cloning Third Edition, Cold Spring Harbor Laboratory Press). The introduction of deletion was confirmed by sequencing the phage DNA sequence. DNA sequencing was performed in the same manner as Example 1. The binding ability to titanium of the obtained point mutants was measured by the method shown in Example 2, by adjusting the phage amount added to $10^{10}$ pfu. The binding ability to titanium of both deletion mutants are shown in FIG. 11. From FIG. 11, it has been revealed that phage clone expressing a peptide shown in SEQ ID NO: 1 that binds to titanium bind with the same strength for 1 to 6th in the first part.

EXAMPLE 6

From the result of Example 4, it has been revealed that the positive charge of the side chain of the first arginine of SEQ ID NO: 1 plays an important role in the binding to titanium. However, as the arginine is located at the amino-terminal, it has a positively charged amino group at the end of the main chain. In order to investigate the possibility of that the positive charge works by cooperating with the positive charge of the side chain, an insertion mutant wherein alanine is introduced before arginine was prepared and the influence to the binding ability to titanium was examined.

Preparation of the insertion mutant was performed by the same method as Example 4, except for annealing condition. Annealing was performed at 85° C. for 10 min, at 48° C. for 15 min, and then the switch of heat block (ALB121, IWAKI) was turned off and left until being cool down to room temperature. The sequence of the primer used (SEQ ID NO: 54) is shown in FIG. 8. The introduction of insert mutation was confirmed by sequencing the phage DNA sequence. DNA sequencing was performed in the same manner as Example 1. The binding ability to titanium of the obtained insert mutant was measured according to the method shown in Example 2 by adjusting the phage level added to $10^{10}$ pfu. The binding ability to titanium of insert mutant is shown in FIG. 11.

The results of Example 6 show that it is not always necessary for arginine to be at the head for the binding of SEQ ID NO: 15 to titanium. This is an important knowledge showing that when preparing chimeric protein, artificial protein or synthetic peptide binding to titanium, there is no limitation for the placement of SEQ ID NO: 1 or 3.

EXAMPLE 7

From the results of Examples 3 to 6, it can be estimated that the phage clone expressing a peptide shown in SEQ ID NO: 3 is bound to a hydroxy group bound to titanium atom, being charged. Therefore, to increase hydroxy groups binding to titanium surface, the binding ability of phage clone expressing a peptide shown in SEQ ID NO: 3, to titanium particles treated with hydrogen peroxide. 10 mg of titanium particles (particle diameter under 150 mm; Sumitomo titanium) was put into Eppendorf tube, 1 ml of 3% hydrogen peroxide (Wako Pure Chemical) was added. The mixture was incubated at 120° C., 80° C., room temperature (RT) for 1 hour, respectively and washed twice with TBS. The binding ability of phage clone expressing a peptide shown in SEQ ID NO: 3 was measured by the method shown in Example 2, by adjusting the phage amount added to $10^{10}$ pfu. The influence of the hydrogen peroxide treatment on phage binding ability is shown in FIG. 12.

From the results of Example 7, it is revealed that by the hydrogen peroxide treatment, the binding level of phage clone expressing a peptide shown in SEQ ID NO: 3 can be increased. Therefore, by changing the titanium surface condition, the possibility to control the binding level of phage is suggested.

EXAMPLE 8

To investigate the binding specificity of phage clone expressing a peptide comprising an amino acid sequence shown in SEQ ID NO: 3 to metal material, to 10 mg each of gold (purity>99.9%, particle diameter<150 μm)/silver (purity>99.9%, particle diameter<75 μm)/copper (purity>99%, particle diameter 75-150 μm)/platinum (purity>99.9%, particle diameter<75 μm)/iron (purity>99.9%, particle diameter<150 μm)/tin (purity>99.9%, particle diameter<150 μm)/zinc (purity>99.9%, particle diameter<150 μm)/chrome (purity>98%, particle diameter>10 μm)/cobalt (purity>99%, particle diameter<75 μm)/silicon (purity>99%, particle diameter<150 μm) (Kojundo Chemical Lab., Saitama), the binding ability to each metal was examined by the same method of Example 2, by using $10^{10}$ pfu/ml of phage clone expressing a peptide comprising an amino acid sequence shown in SEQ ID NO: 3. The results are shown in FIG. 13.

From the results shown in FIG. 13, it has been revealed that phage clone expressing a peptide comprising an amino acid sequence shown in SEQ ID NO: 2 binds not only to titanium, but also to silver or silicon.

EXAMPLE 9

In order to confirm whether the binding form to silver or silicone, and the sequence specificity of the phage clone expressing a peptide comprising an amino acid sequence shown in SEQ ID NO: 3 is similar as in the case of binding to titanium, the binding ability of the alanine substituted-mutant phage of SEQ ID NOs: 4, 5, 7, 8 used in Example 4 to silver/silicon was examined by the method shown in Example 2. The results are shown in FIG. 14. From the results shown in FIG. 14, the influence of each alanine substitution on the binding ability to silver/silicon showed the same trend as for titanium. From this result, it was suggested that phage clone expressing SEQ ID NO: 3 binds to silver/silicone with the same molecular mechanism and sequence specificity when binding to titanium.

EXAMPLE 10

In order to confirm whether the synthetic peptide comprising an amino acid sequence shown in SEQ ID NO: 3 binds to titanium surface, the binding ability of the synthetic peptides comprising an amino acid sequence shown in SEQ ID NO: 3 to titanium particles was examined. 10 mg of titanium particles used in Example 1 was put into an Eppendorf tube, washed twice with 50 mM HEPES-NaOH, 150 mM NaCl. Then, 100 μl of 5 to 40 μM of the synthetic peptides of SEQ ID NO: 3, and the mixture was stirred by rotating by using a rotary shaker rotator RT-50 (Taitec) at room temperature for 2 hours. By centrifuging with a desk-top centrifuge H-1300 (Kokusan, Tokyo), at 13,000 rpm, for 5 sec., the supernatant was removed, mixed with fluoro aldehyde (Pias Rockford, Ill.), and by using a spectrofluorometer (Nippon Bunko, Tokyo), at excitation wave length 342 nm, fluorescent wave length 437 nm, the binding level to titanium was calculated from the peptide concentration of the supernatant. The relative surface area of titanium was calculated from the density and mean particle diameter. Further, the binding ability of the synthetic peptide comprising an amino acid sequence shown in SEQ ID NO: 2 to silicone/tin used in Example 13 was examined by the same method. Fitting with Langmuir adsoprion isotherm was performed to the obtained results, and the maximum adsorption level/dissociation constant obtained are shown in Table 1.

TABLE 1

|    | Kd (μM)     | qm (mole/m$^2$)          |
|----|-------------|--------------------------|
| Ti | 11.1 ± 2.8  | 2.5 ± 0.3 × $10^{-6}$    |
| Si | 13.2 ± 4.0  | 2.1 ± 0.3 × $10^{-7}$    |
| Sn | ND          | ND                       |

EXAMPLE 11

Most of the times, inorganic material-binding peptides have a biomineralization ability of the target material. Therefore, the biomineralization ability of silver of the synthetic peptide comprising an amino acid sequence shown in SEQ ID NO: 3 was examined by the following method. To 0.1 to 0.4 mM of synthetic peptide comprising an amino acid sequence shown in SEQ ID NO: 3 dissolved in TBS, aqueous silver nitrate solution was added so that the final concentration becomes 0.1 mM. The mixture was then incubated for 48 hours at 25° C., and the generated silver was recovered by centrifugation. The recovered silver was washed well with distilled water, and observed with a transmission electron microscopy. The results are shown in FIG. 15. From the results shown in FIG. 15, it can be seen that crystalline particles with a size of about 500 nm, were generated from synthetic peptide comprising an amino acid sequence shown in SEQ ID NO: 3.

EXAMPLE 12

The biomineralization ability of silicon of the synthetic peptide comprising an amino acid sequence shown in SEQ ID NO; 3 was examined by the following method. To 2 to 12 mg/ml of synthetic peptide comprising an amino acid sequence shown in SEQ ID NO: 3 dissolved in TBS or PBS, ¹/₁₀ volume of tetramethoxysilane (Shin-Etsu Chemical, Tokyo) diluted with 1 mM HCl so that the final concentration becomes 0.1 M was added, left stand for 5 min at room temperature. Then, the generated silica was recovered by centrifugation. The recovered silica was washed well with distilled water, and dissolved by incubation with 20 μl of 0.5 N NaOH, at 98° C. for 30 min. To 250 μl of solution diluted to 100 to 500 fold with distilled water, 10 μl of 10-fold diluted sulfuric acid for measuring toxic metal, 10 μl of 10% aqueous ammonium molybdate solution were added. The mixture was incubated at 25° C. for 10 min, and the generated silica level was determined from 385 nm optical density. The results are shown in FIG. 16. The morphology of the generated silica observed by transmission electron microscopy and scanning electron microscopy is shown in FIG. 17. From these results, it has been revealed that the synthetic peptide comprising an amino acid sequence shown in SEQ ID NO: 3 has a biomineralization ability of silica particles.

EXAMPLE 13

In order to show that the fusion protein having a peptide sequence comprising an amino acid sequence shown in SEQ ID NO: 1 acquires a titanium binding ability, a fusion protein fusing SEQ ID NO: 1 to ferritin protein (hereinafter, TBF) was prepared. Plasmid construction to express TBF was performed by the method shown schematically in FIG. 18. In other words, as for the peptide-fused recombinant ferritin-expressing vector comprising an amino acid sequence shown in SEQ ID NO: 1 was prepared as follows: horse recombinant ferritin-expressing vector, pMK2/ferritin, was cleaved with restriction enzymes BamHI and SacI; annealed synthetic DNAs shown in SEQ ID NOs: 55 and 56 were introduced, and cleaved with BamHI. A short DNA fragment generated when pMK2/ferritin is cleaved with BamHI was introduced thereto.

The constructed TBF expressing plasmid was transfected to *E. coli* XLI-blue strain according to a common procedure (Molecular Cloning Third Edition, Cold Spring Harbor Laboratory Press). Transfected strains were precultured in 5 ml LB medium containing 100 μg/ml carbenicillin for 16 to 20 hours, at 37° C., subcultured to 500 ml LB medium containing 100 μg/ml carbenicillin, and further cultured at 37° C. for 16 to 18 hours. After harvesting *E. coli* by centrifugation, the strains were washed with 50 mM Tris HCl pH 8.0 buffer, and dispersed well with 20 ml of 50 mM Tris HCl pH 8.0 per 1 liter of cultured strain. Then, the resultant was homogenized with ultrasonic homogenizer Sonifer 250 (Branson, Danbury, Conn.), micro tip, output 7, duty cycle 50%, for 2 min. Afterwards, the operation of ice-cold, 2 min-homogenize, ice-cold was repeated, and the strains were homogenized well. After homogenization, soluble fractions were recovered by centrifugation, bathed at 70° C. for 15 min, left stand at room temperature for cooling down gradually, and the supernatant was recovered by centrifugation. The recovered solution was purified by column chromatography by using Q-Sepharose HP (Amersham, Piscataway, N.J.), an anion exchange carrier. TBF was eluted by gradient of 0 to 400 mM sodium chloride. The eluted TBF was concentrated by ultrafiltration, and then elution peak of 24-meric of TBS was recovered by gel filtration chromatography by using Sephacryl S-400 (Amersham, Piscataway, N.J.) as a resin.

The binding ability to titanium of this TBF was measured by QCM used in Example 3. As a control, the contribution of the binding to titanium other than SEQ ID NO:1, the binding to titanium of recombinant ferritin protein (fer 0) that do not comprise a peptide comprising an amino acid sequence shown in SEQ ID NO:1 was examined. The results are shown in FIG. 19. From the results shown in FIG. 19, it has been revealed that TBF binds more strongly to titanium than fer 0, and that the affinity to titanium of the fusion protein containing a peptide comprising an amino acid sequence shown in SEQ ID NO:1 increases significantly.

INDUSTRIAL APPLICABILITY

The present invention provides a titanium complex that can be used advantageously, for example in medical field comprising a titanium implant material that shortens the osseointegration period, a titanium implant material with high resistance to bacterial infection by mimicking teeth, or an oxidized titanium material with photocatalystic activity that can be used in visible light region, in nano biotechnology, material engineering, semiconductors, medical agents and cosmetics.

The invention claimed is:

1. A titanium binding peptide consisting of the amino acid sequence of SEQ ID NO: 1.

2. A titanium binding peptide consisting of the amino acid sequence of SEQ ID NO: 2.

3. A titanium binding peptide comprising the amino acid sequence of SEQ ID NO: 3.

4. A titanium binding peptide comprising any one of the amino acid sequences of SEQ ID NOs: 4 to 14.

5. A titanium binding peptide comprising the amino acid sequence of SEQ ID NO: 15.

6. A titanium binding peptide comprising any one of the amino acid sequences of SEQ ID NOs: 16 to 24.

7. A titanium binding peptide comprising any one of the amino acid sequences of SEQ ID NOs: 25 to 38.

8. The titanium binding peptide according to claim 1, being chemically modified.

9. The titanium binding peptide according to claim 1, wherein titanium is a metal titanium, a titanium alloy or a titanium dioxide.

10. A titanium-peptide complex, wherein the titanium binding peptide according to claim 1 is bound to titanium.

11. An artificial titanium binding protein comprising the titanium binding peptide according to claim 1 conjugated, with a functional protein, wherein the functional protein is ferritin.

12. A titanium-artificial protein complex, wherein the artificial protein according to claim 11 is bound to titanium.

13. A titanium binding chimeric protein comprising the titanium binding peptide according to claim 1 conjugated, with a labeled substance, a peptide tag, or a nonpeptide compound, wherein the nonpeptide compound is an antibiotic, a fluorescein, a rhodamine, polystyrene, polypropylene, polyethylene, a glass bead, a silicagel, a polysaccharide, a polysaccharide delivative, or a polyalkylene glycol.

14. A titanium-chimeric protein complex, wherein the chimeric protein according to claim 13 is bound to titanium.

15. A titanium binding phage expressing the titanium binding peptide according to claim 1 on the particle surface.

16. A titanium-phage complex, wherein the phage according to claim 15 is bound to titanium.

17. A silver binding peptide consisting of the amino acid sequence of SEQ ID NO: 1.

18. A silver binding peptide consisting of the amino acid sequence of SEQ ID NO: 2.

19. A silver binding peptide comprising the amino acid sequence of SEQ ID NO: 3.

20. The silver binding peptide according to claim 17, 18 or 19, being chemically modified.

21. A silver-peptide complex, wherein the silver binding peptide according to claim 17, 18 or 19 is bound to silver.

22. A silver binding artificial protein comprising the silver binding peptide according to claim 17, 18 or 19 conjugated with a functional protein, wherein the functional protein is ferritin.

23. A silver-artificial protein complex, wherein the artificial protein according to claim 22 is bound to silver.

24. A silver binding chimeric protein comprising the silver binding peptide according to claim 17, 18 or 19 conjugated with a labeled substance, a peptide tag, or a nonpeptide compound, wherein the nonpeptide compound is an antibiotic, a fluorescein, a rhodamine, polystyrene, polypropylene, polyethylene, a glass bead, a silicagel, a polysaccharide, a polysaccharide delivative, or a polyalkylene glycol.

25. A silver-chimeric protein complex, wherein the chimeric protein according to claim 24 is bound to silver.

26. A silver binding phage expressing the silver binding peptide according to claim 17, 18 or 19 on the particle surface.

27. A silver-phage complex, wherein the phage according to claim 26 is bound to silver.

28. A silicon binding peptide consisting of the amino acid sequence of SEQ ID NO: 1.

29. A silicon binding peptide consisting of the amino acid sequence of SEQ ID NO: 2.

30. A silicon binding peptide comprising the amino acid sequence of SEQ ID NO: 3.

31. The silicon binding peptide according to claim 28, 29 or 30, being chemically modified.

32. A silicon-peptide complex, wherein the silicon binding peptide according to claim 28, 29 or 30 is bound to silicon.

33. A silicon binding artificial protein comprising the silicon binding peptide according to claim 28, 29 or 30 conjugated with a functional protein, wherein the functional protein is ferritin.

34. A silicon-artificial protein complex, wherein the artificial protein according to claim 33 is bound to silicon.

35. A silicon binding chimeric protein comprising the silicon binding peptide according to claim 28, 29 or 30 conjugated, with a labeled substance, a peptide-tag, or a nonpeptide compound, wherein the nonpeptide compound is an antibiotic, a fluorescein, a rhodamine, polystyrene, polypropylene, polyethylene, a glass bead, a silicagel, a polysaccharide, a polysaccharide delivative, or a polyalkylene glycol.

36. A silicon-chimeric protein complex wherein the chimeric protein according to claim 35 is bound to silicon.

37. A silicon binding phage expressing the silicon binding peptide according to claim 28, 29 or 30 on the particle surface.

38. A silicon-phage complex, wherein the phage according to claim 37 is bound to silicon.

* * * * *

SEQUENCE LISTING

<160> NUMBER OF SEQ ID NOS: 56

<210> SEQ ID NO 1
<211> LENGTH: 6
<212> TYPE: PRT
<213> ORGANISM: Artificial Sequence
<220> FEATURE:
<223> OTHER INFORMATION: chemically synthesized

<400> SEQUENCE: 1

```
Arg Lys Leu Pro Asp Ala
1               5

<210> SEQ ID NO 2
<211> LENGTH: 6
<212> TYPE: PRT
<213> ORGANISM: Artificial Sequence
<220> FEATURE:
<223> OTHER INFORMATION: chemically synthesized

<400> SEQUENCE: 2

Arg Ala Leu Pro Asp Ala
1               5

<210> SEQ ID NO 3
<211> LENGTH: 12
<212> TYPE: PRT
<213> ORGANISM: Artificial Sequence
<220> FEATURE:
<223> OTHER INFORMATION: chemically synthesized

<400> SEQUENCE: 3

Arg Lys Leu Pro Asp Ala Pro Gly Met His Thr Trp
1               5                   10

<210> SEQ ID NO 4
<211> LENGTH: 12
<212> TYPE: PRT
<213> ORGANISM: Artificial Sequence
<220> FEATURE:
<223> OTHER INFORMATION: chemically synthesized

<400> SEQUENCE: 4

Ala Lys Leu Pro Asp Ala Pro Gly Met His Thr Trp
1               5                   10

<210> SEQ ID NO 5
<211> LENGTH: 12
<212> TYPE: PRT
<213> ORGANISM: Artificial Sequence
<220> FEATURE:
<223> OTHER INFORMATION: chemically synthesized

<400> SEQUENCE: 5

Arg Ala Leu Pro Asp Ala Pro Gly Met His Thr Trp
1               5                   10

<210> SEQ ID NO 6
<211> LENGTH: 12
<212> TYPE: PRT
<213> ORGANISM: Artificial Sequence
<220> FEATURE:
<223> OTHER INFORMATION: chemically synthesized

<400> SEQUENCE: 6

Arg Lys Leu Pro Asp Ala Pro Gly Met His Thr Trp
1               5                   10

<210> SEQ ID NO 7
<211> LENGTH: 12
<212> TYPE: PRT
<213> ORGANISM: Artificial Sequence
<220> FEATURE:
<223> OTHER INFORMATION: chemically synthesized

<400> SEQUENCE: 7

Arg Lys Leu Ala Asp Ala Pro Gly Met His Thr Trp
```

```
<210> SEQ ID NO 8
<211> LENGTH: 12
<212> TYPE: PRT
<213> ORGANISM: Artificial Sequence
<220> FEATURE:
<223> OTHER INFORMATION: chemically synthesized

<400> SEQUENCE: 8

Arg Lys Leu Pro Ala Ala Pro Gly Met His Thr Trp
1               5                   10

<210> SEQ ID NO 9
<211> LENGTH: 12
<212> TYPE: PRT
<213> ORGANISM: Artificial Sequence
<220> FEATURE:
<223> OTHER INFORMATION: chemically synthesized

<400> SEQUENCE: 9

Arg Lys Leu Pro Asp Ala Ala Gly Met His Thr Trp
1               5                   10

<210> SEQ ID NO 10
<211> LENGTH: 12
<212> TYPE: PRT
<213> ORGANISM: Artificial Sequence
<220> FEATURE:
<223> OTHER INFORMATION: chemically synthesized

<400> SEQUENCE: 10

Arg Lys Leu Pro Asp Ala Pro Ala Met His Thr Trp
1               5                   10

<210> SEQ ID NO 11
<211> LENGTH: 12
<212> TYPE: PRT
<213> ORGANISM: Artificial Sequence
<220> FEATURE:
<223> OTHER INFORMATION: chemically synthesized

<400> SEQUENCE: 11

Arg Lys Leu Pro Asp Ala Pro Gly Ala His Thr Trp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: chemically synthesized

<400> SEQUENCE: 12

Arg Lys Leu Pro Asp Ala Pro Gly Met Ala Thr Trp
1               5                   10

<210> SEQ ID NO 13
<211> LENGTH: 12
<212> TYPE: PRT
<213> ORGANISM: Artificial Sequence
<220> FEATURE:
<223> OTHER INFORMATION: chemically synthesized

<400> SEQUENCE: 13

Arg Lys Leu Pro Asp Ala Pro Gly Met His Ala Trp
1               5                   10
```

```
<210> SEQ ID NO 14
<211> LENGTH: 12
<212> TYPE: PRT
<213> ORGANISM: Artificial Sequence
<220> FEATURE:
<223> OTHER INFORMATION: chemically synthesized

<400> SEQUENCE: 14

Arg Lys Leu Pro Asp Ala Pro Gly Met His Thr Ala
1               5                   10

<210> SEQ ID NO 15
<211> LENGTH: 13
<212> TYPE: PRT
<213> ORGANISM: Artificial Sequence
<220> FEATURE:
<223> OTHER INFORMATION: chemically synthesized

<400> SEQUENCE: 15

Ala Arg Lys Leu Pro Asp Ala Pro Gly Met His Thr Trp
1               5                   10

<210> SEQ ID NO 16
<211> LENGTH: 12
<212> TYPE: PRT
<213> ORGANISM: Artificial Sequence
<220> FEATURE:
<223> OTHER INFORMATION: chemically synthesized

<400> SEQUENCE: 16

Leu Asp Thr Thr Gln Val Ser Gly Pro Met Ser Ser
1               5                   10

<210> SEQ ID NO 17
<211> LENGTH: 12
<212> TYPE: PRT
<213> ORGANISM: Artificial Sequence
<220> FEATURE:
<223> OTHER INFORMATION: chemically synthesized

<400> SEQUENCE: 17

Ser Tyr Arg Leu Pro Val Tyr Leu His Ala Leu Leu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: chemically synthesized

<400> SEQUENCE: 18

Ser Asp Pro Gln Gln Asp Trp Arg Arg Thr Thr Pro
1               5                   10

<210> SEQ ID NO 19
<211> LENGTH: 12
<212> TYPE: PRT
<213> ORGANISM: Artificial Sequence
<220> FEATURE:
<223> OTHER INFORMATION: chemically synthesized

<400> SEQUENCE: 19

Leu Pro Ser Gln Leu Leu Ser Gln Val Gln Leu Thr
1               5                   10
```

-continued

```
<210> SEQ ID NO 20
<211> LENGTH: 12
<212> TYPE: PRT
<213> ORGANISM: Artificial Sequence
<220> FEATURE:
<223> OTHER INFORMATION: chemically synthesized

<400> SEQUENCE: 20

Leu Cys Ala Gln Gln Thr Thr Ser Val His Pro Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: chemically synthesized

<400> SEQUENCE: 21

Met Gln Met Glu Gly Lys Pro Thr Leu Thr Leu Arg
1               5                   10

<210> SEQ ID NO 22
<211> LENGTH: 12
<212> TYPE: PRT
<213> ORGANISM: Artificial Sequence
<220> FEATURE:
<223> OTHER INFORMATION: chemically synthesized

<400> SEQUENCE: 22

Ser Thr Leu Lys Gln Pro Ile Gln Leu Leu Ala Gln
1               5                   10

<210> SEQ ID NO 23
<211> LENGTH: 12
<212> TYPE: PRT
<213> ORGANISM: Artificial Sequence
<220> FEATURE:
<223> OTHER INFORMATION: chemically synthesized

<400> SEQUENCE: 23

Ser Cys His Val Trp Tyr Asp Ser Cys Ser Ser Pro
1               5                   10

<210> SEQ ID NO 24
<211> LENGTH: 12
<212> TYPE: PRT
<213> ORGANISM: Artificial Sequence
<220> FEATURE:
<223> OTHER INFORMATION: chemically synthesized

<400> SEQUENCE: 24

Gln Asp Met Ile Arg Thr Ser Ala Leu Met Leu Gln
1               5                   10

<210> SEQ ID NO 25
<211> LENGTH: 9
<212> TYPE: PRT
<213> ORGANISM: Artificial Sequence
<220> FEATURE:
<223> OTHER INFORMATION: chemically synthesized

<400> SEQUENCE: 25

Cys Thr Ser Pro Thr Ser Val Asp Cys
1               5
```

<210> SEQ ID NO 26
<211> LENGTH: 9
<212> TYPE: PRT
<213> ORGANISM: Artificial Sequence
<220> FEATURE:
<223> OTHER INFORMATION: chemically synthesized

<400> SEQUENCE: 26

Cys Thr Pro Ser Pro His Gln Gly Cys
1               5

<210> SEQ ID NO 27
<211> LENGTH: 9
<212> TYPE: PRT
<213> ORGANISM: Artificial Sequence
<220> FEATURE:
<223> OTHER INFORMATION: chemically synthesized

<400> SEQUENCE: 27

Cys His Thr Ala Pro Leu Pro Arg Cys
1               5

<210> SEQ ID NO 28
<211> LENGTH: 9
<212> TYPE: PRT
<213> ORGANISM: Artificial Sequence
<220> FEATURE:
<223> OTHER INFORMATION: chemically synthesized

<400> SEQUENCE: 28

Cys His Gly Ala Thr Pro Gln Asn Cys
1               5

<210> SEQ ID NO 29
<211> LENGTH: 9
<212> TYPE: PRT
<213> ORGANISM: Artificial Sequence
<220> FEATURE:
<223> OTHER INFORMATION: chemically synthesized

<400> SEQUENCE: 29

Cys Ser Gly His Asn Pro Thr His Cys
1               5

<210> SEQ ID NO 30
<211> LENGTH: 9
<212> TYPE: PRT
<213> ORGANISM: Artificial Sequence
<220> FEATURE:
<223> OTHER INFORMATION: chemically synthesized

<400> SEQUENCE: 30

Cys Pro Met Trp Gln Ala Gln Gln Cys
1               5

<210> SEQ ID NO 31
<211> LENGTH: 9
<212> TYPE: PRT
<213> ORGANISM: Artificial Sequence
<220> FEATURE:
<223> OTHER INFORMATION: chemically synthesized

<400> SEQUENCE: 31

Cys Gly Tyr Tyr Ser Met Ser His Cys
1               5

<210> SEQ ID NO 32

```
<211> LENGTH: 9
<212> TYPE: PRT
<213> ORGANISM: Artificial Sequence
<220> FEATURE:
<223> OTHER INFORMATION: chemically synthesized

<400> SEQUENCE: 32

Cys Asp Met Leu Thr Pro Arg Ser Cys
1               5

<210> SEQ ID NO 33
<211> LENGTH: 9
<212> TYPE: PRT
<213> ORGANISM: Artificial Sequence
<220> FEATURE:
<223> OTHER INFORMATION: chemically synthesized

<400> SEQUENCE: 33

Cys Leu Arg Leu Gln Ser Gln Asp Cys
1               5

<210> SEQ ID NO 34
<211> LENGTH: 9
<212> TYPE: PRT
<213> ORGANISM: Artificial Sequence
<220> FEATURE:
<223> OTHER INFORMATION: chemically synthesized

<400> SEQUENCE: 34

Cys Gln Ile Thr Trp His His Thr Cys
1               5

<210> SEQ ID NO 35
<211> LENGTH: 9
<212> TYPE: PRT
<213> ORGANISM: Artificial Sequence
<220> FEATURE:
<223> OTHER INFORMATION: chemically synthesized

<400> SEQUENCE: 35

Cys Ser Ala His His His Asp Lys Cys
1               5

<210> SEQ ID NO 36
<211> LENGTH: 9
<212> TYPE: PRT
<213> ORGANISM: Artificial Sequence
<220> FEATURE:
<223> OTHER INFORMATION: chemically synthesized

<400> SEQUENCE: 36

Cys Met Thr Lys Asn Pro Leu Asn Cys
1               5

<210> SEQ ID NO 37
<211> LENGTH: 9
<212> TYPE: PRT
<213> ORGANISM: Artificial Sequence
<220> FEATURE:
<223> OTHER INFORMATION: chemically synthesized

<400> SEQUENCE: 37

Cys Lys Thr Ser Leu Pro Thr Thr Cys
1               5

<210> SEQ ID NO 38
<211> LENGTH: 9
```

```
<212> TYPE: PRT
<213> ORGANISM: Artificial Sequence
<220> FEATURE:
<223> OTHER INFORMATION: chemically synthesized

<400> SEQUENCE: 38

Cys Val Ser Thr Tyr Trp Lys Thr Cys
1               5

<210> SEQ ID NO 39
<211> LENGTH: 20
<212> TYPE: DNA
<213> ORGANISM: Artificial Sequence
<220> FEATURE:
<223> OTHER INFORMATION: chemically synthesized

<400> SEQUENCE: 39
ccctcatagt tagcgtaacg                                               20

<210> SEQ ID NO 40
<211> LENGTH: 25
<212> TYPE: DNA
<213> ORGANISM: Artificial Sequence
<220> FEATURE:
<223> OTHER INFORMATION: chemically synthesized

<400> SEQUENCE: 40
aggcagcttc gcagagtgag aatag                                         25

<210> SEQ ID NO 41
<211> LENGTH: 24
<212> TYPE: DNA
<213> ORGANISM: Artificial Sequence
<220> FEATURE:
<223> OTHER INFORMATION: chemically synthesized

<400> SEQUENCE: 41
catcaggcag cgcccgagag tgag                                          24

<210> SEQ ID NO 42
<211> LENGTH: 24
<212> TYPE: DNA
<213> ORGANISM: Artificial Sequence
<220> FEATURE:
<223> OTHER INFORMATION: chemically synthesized

<400> SEQUENCE: 42
ggagcatcag gcgccttccg agag                                          24

<210> SEQ ID NO 43
<211> LENGTH: 25
<212> TYPE: DNA
<213> ORGANISM: Artificial Sequence
<220> FEATURE:
<223> OTHER INFORMATION: chemically synthesized

<400> SEQUENCE: 43
ccgggagcat cagccagctt ccgag                                         25

<210> SEQ ID NO 44
<211> LENGTH: 24
<212> TYPE: DNA
<213> ORGANISM: Artificial Sequence
<220> FEATURE:
<223> OTHER INFORMATION: chemically synthesized

<400> SEQUENCE: 44
```
atcccgggag cagcaggcag cttc                                                24

<210> SEQ ID NO 45
<211> LENGTH: 25
<212> TYPE: DNA
<213> ORGANISM: Artificial Sequence
<220> FEATURE:
<223> OTHER INFORMATION: chemically synthesized

<400> SEQUENCE: 45
gtatgcatcc cggcagcatc aggca                                               25

<210> SEQ ID NO 46
<211> LENGTH: 24
<212> TYPE: DNA
<213> ORGANISM: Artificial Sequence
<220> FEATURE:
<223> OTHER INFORMATION: chemically synthesized

<400> SEQUENCE: 46
agtatgcatc gcgggagcat cagg                                                24

<210> SEQ ID NO 47
<211> LENGTH: 26
<212> TYPE: DNA
<213> ORGANISM: Artificial Sequence
<220> FEATURE:
<223> OTHER INFORMATION: chemically synthesized

<400> SEQUENCE: 47
ccccaagtat gcgccccggg agcatc                                              26

<210> SEQ ID NO 48
<211> LENGTH: 25
<212> TYPE: DNA
<213> ORGANISM: Artificial Sequence
<220> FEATURE:
<223> OTHER INFORMATION: chemically synthesized

<400> SEQUENCE: 48
tccaccccaa gtagccatcc cggga                                               25

<210> SEQ ID NO 49
<211> LENGTH: 23
<212> TYPE: DNA
<213> ORGANISM: Artificial Sequence
<220> FEATURE:
<223> OTHER INFORMATION: chemically synthesized

<400> SEQUENCE: 49
tccaccccaa gcatgcatcc cgg                                                 23

<210> SEQ ID NO 50
<211> LENGTH: 23
<212> TYPE: DNA
<213> ORGANISM: Artificial Sequence
<220> FEATURE:
<223> OTHER INFORMATION: chemically synthesized

<400> SEQUENCE: 50
aacctccacc cgcagtatgc atc                                                 23

<210> SEQ ID NO 51
<211> LENGTH: 29
<212> TYPE: DNA

```
<213> ORGANISM: Artificial Sequence
<220> FEATURE:
<223> OTHER INFORMATION: chemically synthesized

<400> SEQUENCE: 51
ggaggatccg ccgaaactgt tgaaagttg                                              29

<210> SEQ ID NO 52
<211> LENGTH: 35
<212> TYPE: DNA
<213> ORGANISM: Artificial Sequence
<220> FEATURE:
<223> OTHER INFORMATION: chemically synthesized

<400> SEQUENCE: 52
gggggatcct ccaccagcat caggcagctt ccgag                                       35

<210> SEQ ID NO 53
<211> LENGTH: 35
<212> TYPE: DNA
<213> ORGANISM: Artificial Sequence
<220> FEATURE:
<223> OTHER INFORMATION: chemically synthesized

<400> SEQUENCE: 53
gggggatcct ccaccagcat caggcagcgc ccgag                                       35

<210> SEQ ID NO 54
<211> LENGTH: 39
<212> TYPE: DNA
<213> ORGANISM: Artificial Sequence
<220> FEATURE:
<223> OTHER INFORMATION: chemically synthesized

<400> SEQUENCE: 54
agcatcaggc agcttccgtg cagagtgaga atagaaagg                                   39

<210> SEQ ID NO 55
<211> LENGTH: 21
<212> TYPE: DNA
<213> ORGANISM: Artificial Sequence
<220> FEATURE:
<223> OTHER INFORMATION: chemically synthesized

<400> SEQUENCE: 55
tatgcgcaaa cttccggatg c                                                      21

<210> SEQ ID NO 56
<211> LENGTH: 21
<212> TYPE: DNA
<213> ORGANISM: Artificial Sequence
<220> FEATURE:
<223> OTHER INFORMATION: chemically synthesized

<400> SEQUENCE: 56
tagcatccgg aagtttgcgc a                                                      21
```